(12) United States Patent
Imamoto et al.

(10) Patent No.: US 7,109,702 B2
(45) Date of Patent: Sep. 19, 2006

(54) NON-DESTRUCTIVE INSPECTION METHOD

(75) Inventors: Kazunobu Imamoto, Osaka (JP); Takashi Kimura, Aichi (JP)

(73) Assignees: Daihatsu Motor Co., Ltd., Osaka (JP); Magnegraph Co., Ltd., Aichi (JP)

( * ) Notice: Subject to any disclaimer, the term of this patent is extended or adjusted under 35 U.S.C. 154(b) by 92 days.

(21) Appl. No.: 10/490,725

(22) PCT Filed: Sep. 24, 2002

(86) PCT No.: PCT/JP02/09800

§ 371 (c)(1),
(2), (4) Date: Jun. 30, 2004

(87) PCT Pub. No.: WO03/027661

PCT Pub. Date: Mar. 4, 2003

(65) Prior Publication Data
US 2005/0122099 A1  Jun. 9, 2005

(30) Foreign Application Priority Data
Sep. 25, 2001 (JP) ............................. 2001-292330

(51) Int. Cl.
*G01N 27/72* (2006.01)
*G01N 27/82* (2006.01)
*G01R 33/12* (2006.01)

(52) U.S. Cl. ...................... 324/240; 324/242
(58) Field of Classification Search ................ 324/240, 324/242
See application file for complete search history.

(56) References Cited
U.S. PATENT DOCUMENTS
6,232,774 B1  5/2001  Kimura

FOREIGN PATENT DOCUMENTS
| JP | 10-26609 | 1/1998 |
| JP | 2000-227418 | 8/2000 |
| JP | 2001-165911 | 6/2001 |

OTHER PUBLICATIONS
English translation of NPL document Kimura et al. "Nugget profiler" Inspection Engineering, vol. 6, No. 6, pp. 50-54 (Jun. 1, 2001).*
Kimura et al. "Nugget Profiler". *Inspection Engineering*, vol. 6, No. 6, pp. 50-54 (Jun. 1, 2001).

* cited by examiner

*Primary Examiner*—Reena Aurora
(74) *Attorney, Agent, or Firm*—Hamre, Schumann, Mueller & Larson, P.C.

(57) ABSTRACT

A non-destructive inspection includes: magnetizing a target by a first magnetostatic field (S2); shutting off the magnetostatic field (S3); measuring, at measurement points, the transient change of a differential magnetic flux density of a first residual magnetic field of the target (S4); obtaining a first time constant by the main time constant of the transient change at each measurement point (S5); magnetizing the target by a second magnetostatic field (S2); shutting off the second field (S3); measuring, at the measurement points, the transient change of a differential magnetic flux density of a second residual magnetic field of the target (S4); obtaining a second time constant by the main time constant of the transient change for each measurement point (S5); and obtaining information about the internal structure of the target by the distribution differences between the first and the second time constants at the measurement points (S7).

8 Claims, 17 Drawing Sheets

NON-DESTRUCTIVE INSPECTION METHOD

TECHNICAL FIELD

The present invention relates to a non-destructive inspection method for determining e.g. the welding quality of a spot weld section.

BACKGROUND ART

Spot welding is a known welding technology for welding together metal plates, which can be used in the manufacture of automobiles, domestic electrical products, and the like. In spot welding, firstly, as illustrated in FIG. 18, two superimposed metal plates 100a, 100b are sandwiched between a pair of electrodes 150a, 150b. In this state, pressure is applied locally to the metal plates 100a, 100b by means of the pair of electrodes 150a, 150b, and current is passed between the electrodes 150a, 150b. The current flows in a concentrated manner through the portion of the metal plates 100a, 100b sandwiched between the electrodes 150a, 150b, and therefore generates Joule heat. A portion of the metal plates 100a, 100b is melted by this Joule heat, whereupon, the passage of current is halted. When the molten portion of the metal plates 100a, 100b cools and solidifies, the metal plates 100a, 100b will be welded together.

FIG. 19 is a cross-sectional view of a spot welded section of two metal plates 100a, 100b which have been spot welded as described above. In the spot welded section, the outer surfaces of the metal plates 100a, 100b are dented due to the pressure applied by the electrodes 150a, 150b. This denting is called an "indentation" 101, and the length L1 thereof is called the "indentation diameter". A nugget section 102 and a pressure bonded section 103 are formed in the spot weld section. The nugget section 102 in a region where the metal plates 100a, 100b have become unified as a result of being melted due to the application of heat and pressure, and then solidifying. The length L2 of the nugget section 102 is called the "nugget diameter". This nugget diameter L2 greatly influences the welding strength achieved in the spot weld section. The greater the nugget diameter L2, the greater the weld strength of the spot weld section. The pressure bonded section 103 is a region which has received the effects of the applied heat and applied pressure and where the metal plates 100a, 100b have bonded together under pressure. The total length L3 of the nugget section 102 and the pressure bonded section 103 is called the joint diameter. The pressure bonded section 103 is surrounded by a thermally annealed heat affected zone (HAZ) 104. The HAZ 104 has a length L4 called the HAZ diameter. The HAZ 104 is surrounded by an original metal 105 whose metallographic structure has not been affected by the spot welding.

Generally, the nugget diameter L2 or the joint diameter L3 in the spot weld section achieved by welding is appropriately 10 millimeters or less, which is relatively small. Therefore, in many cases, it is necessary to inspect the spot weld section in order to check that it has sufficient weld strength. Since the weld strength of the spot weld section is greatly influenced by the nugget diameter L2, then the nugget diameter L2 can be used effectively as a basis for judging whether or not the spot weld section has a suitable welded state.

Japanese Patent Application Laid-open No. Hei10-26609 discloses inspection technology, one object of which is to measure the nugget diameter L2 in a non-destructive manner, and to judge the suitability or unsuitability of the welded state of a spot weld section on the basis of these measurement results. According to this patent publication, an excitation coil is disposed in the vicinity of an inspection target, and a loop coil forming a sensor is disposed between the inspection target and the excitation coil. In this state, a static magnetic field is generated which passes through the inspection target and the sensor, by passing a DC current through the excitation coil. Thereupon, when the static magnetic field is shut off, the inductance of the loop coil (or a physical quantity that is directly proportional to the inductance thereof) is determined by tracing the course of the loss of the electrical field remaining in the inspection target. This inductance indicates the magnetic permeability of the nugget section 102 and pressure bonded section 103, or the like, constituting the spot welding section through which the residual magnetic field passes. When measurement of this kind is carried out in a plurality of positions with respect to the inspection target, then variation will occur in the plurality of inductances obtained. This variation in inductance reflects variations in the internal structure of the spot weld section. Therefore, the nugget diameter L2 can be estimated by detecting the variations in magnetic permeability, and hence the variations in inductance, caused by changes in the internal structure of the spot weld section, by means of non-destructive inspection technology.

According to the Japanese Patent Application Laid-Open No. 10-26209, the sensor loop coils are arranged to face the indentation 101 at a predetermined distance from the metal sheet 100a or the metal sheet 100b in the non-destructive inspection. Under normal circumstances, air is present at the indentations 101. The magnetic permeability of the air is much smaller than the magnetic permeability of the nugget section 102 or the pressure bonded section 103. Accordingly, the measured loop coil inductance reflects not only the magnetic permeability of the internal structure of the spot weld section but also the magnetic permeability of the air at the indentations 101. If the inductance (or a physical quantity proportional to the inductance) reflects the magnetic permeability of elements other than the internal structure of the spot weld section, the non-destructive inspection of the spot weld section may not give an accurate estimation on the nugget diameter L2.

DISCLOSURE OF THE INVENTION

It is an object of the present invention to provide a non-destructive inspection method capable of giving reliable inspection results in an inspection for e.g. the welding quality of a spot weld section.

According to a first aspect of the present invention, there is provided a non-destructive inspection method including: a step of magnetizing an inspection target by applying a first magnetostatic field to the target; a step of shutting off the first magnetostatic field and measuring transient change in a differential magnetic flux density of a first residual magnetic field passing through the magnetized target, the measuring being performed at a plurality of measurement positions; a step of obtaining a first time constant provided by a main time constant of the transient change for each of the measurement positions; a step of magnetizing the target by applying a second magnetostatic field to the target; a step of shutting off the second magnetostatic field and measuring transient change in a differential magnetic flux density of a second residual magnetic field passing through the magnetized target, the measuring being performed at each of the measurement positions; a step of obtaining a second time constant provided by a main time constant of the transient change for each of the measurement positions; and an information obtaining step of obtaining information about an internal structure of the target based on a difference between distribution of the first time constant and distribution of the second time constant at the measurement positions.

Preferably, the measurement positions may be in a row facing the target.

Preferably, the information about the internal structure in the information obtaining step may be obtained based on a ratio function which is derived from a distribution function of the first time constant with the measurement position as a variable and a distribution function of the second time constant with the measurement position as a variable. Alternatively, the information about the internal structure in the information obtaining step may be obtained based on a difference function which is derived from a distribution function of the first time constant with the measurement position as a variable and a distribution function of the second time constant with the measurement position as a variable.

According to a preferred embodiment, the inspection target may be a spot weld section in a jointed plate member made by spot welding two sheet metals. In this case, the information obtained in the information obtaining step may comprise information about the shape of nugget section included in the spot weld section.

According to a second aspect of the present invention, there is provided another non-destructive inspection method. This method comprises: a scanning step including a cycle of magnetizing a target by applying a magnetostatic field to the target, shutting off the magnetostatic field to measure transient change in a differential magnetic flux density of a residual magnetic field which passes through the magnetized target at a plurality of measurement positions, and obtaining a main time constant of the transient change for each of the measurement positions, the cycle being repeatedly performed for each of a plurality of magnetostatic fields of different magnetic flux densities; and an analyzing step of analyzing a change that the main time constant undergoes at each measurement position as the plurality of magnetostatic fields are changed in the scanning step; and an information obtaining step of obtaining information about an internal structure of the target based on an analysis result obtained by the analyzing step.

Preferably, in the analyzing step, at each of the measurement positions, a magnetic flux density of a critical magnetostatic field may be determined, for which field the change of the main time constant during the scanning step with respect to changes in the magnetostatic field achieves a maximum value. Further, in the information obtaining step, information about the internal structure of the target may be obtained based on a distribution function of the critical magnetostatic field with the measurement positions as a variable.

Preferably, the measurement positions may be in a row facing the target.

Preferably, the target may be a spot weld section in a jointed plate member made by spot welding two sheet metals. In this case, the information about the internal structure obtained in the information obtaining step may comprise information about the shape of a nugget section included in the spot weld section.

Reference is now made to FIG. 1 through FIG. 8 to describe the principles based on which the time constant used in the present invention is calculated. As specifically described below, a magnetostatic field is applied to the inspection target and then shut off. The magnetized inspection target provides a residual magnetic field. At a predetermined position or positions, the transient change of the differential magnetic flux density of the residual field is measured, so that the time constant of the transient change is calculated.

FIG. 1 and FIG. 2 are schematic views showing the general composition of a device for carrying out non-destructive inspection using the application and shutting off of a static magnetic field, and also showing the operation of this device. The non-destructive inspection device comprises an excitation coil 1 wound about an iron core 2, a drive circuit 3 for driving the excitation coil 1, and a plurality of sensor coils 4. The drive circuit 3 incorporates a DC power supply $3a$, a switch $3b$ and a resistance $3c$. The sensor coils 4 are loop coils. When carrying out inspection, this device is positioned in the vicinity of the inspection target. In FIG. 1 and FIG. 2, the device is positioned in the vicinity of the spot weld section of a steel plate member 110, formed by spot welding of two steel plates. A nugget section 102 exists inside this spot weld section.

As shown in FIG. 1, when the switch $3b$ is turned on, a static magnetic field F1 is applied to the spot weld section. More specifically, the switch $3b$ is turned on, a voltage output by the DC power supply $3a$ is applied to the excitation coil 1, and a DC current flows in the excitation coil 1, whereby a static magnetic field F1 is created surrounding the excitation coil 1. A portion of the static magnetic field F1 is formed inside the steel plate member 110. The location in which the magnetic field is formed in the steel plate member 110, in other words, the location through which the magnetic flux passes, is magnetized in accordance with the intensity of the magnetic field. In order to judge the suitability or unsuitability of the state of the welding in the spot weld section, on the basis of the size of the nugget section 102, the non-destructive inspection device is positioned in such a manner that the magnetic flux passes through the nugget section 102 when the static magnetic field is applied.

As shown in FIG. 2, when the switch $3b$ is turned off, the static magnetic field F1 is shut off. More specifically, when the switch $3b$ is turned off, the DC current that has been flowing in the excitation coil 1 until that point is shut off, and therefore the static magnetic field F1 is also shut off. Due to the shutting off of the static magnetic field F1, the loops of magnetic flux of the static magnetic field F1 separate into a closed loop C1 of magnetic flux in the region surrounding the excitation coil 1, and a closed loop C2 of magnetic flux in the region surrounding the steel plate member 110. The closed loop C1 rapidly declines and disappears. By contrast, the closed loop C2 does not disappear immediately, but rather declines in a gradual fashion, due to the sustaining action of the magnetic energy of the steel plate member 110, which is a magnetic body.

During the course of disappearance of the closed loop C2, the change in magnetic flux in the vicinity of the steel plate member 110 is detected by the respective sensor coils 4 positioned in the vicinity of the surface of the steel plate member 110. In an ideal situation, after the static magnetic field has been shut off, the change in magnetic flux detected by the sensor coils 4 decreases in a steady exponential fashion. However, in practice, the situation deviates from this ideal state of change. This deviation is thought to be caused by transient current which is induced in the steel plate member 110 by the change in the state of magnetization in the steel plate member 110, during the course of disappearance of the magnetic energy (residual magnetic field) accumulated in the steel plate member 110. Therefore, the model described below can be hypothesized for the change in the magnetic flux of the residual magnetic field after the static magnetic field has been shut off.

FIG. 3 shows a model of the course of disappearance of the residual magnetic field. In this course of disappearance, as illustrated in FIG. 3, the density of the magnetic flux Φ passing through one of the sensor coils 4 is denoted by B. Furthermore, the plurality of transient currents induced in the steel plate member 110 by the change in the magnetic flux density B are denoted by In1, In2, In3, . . . , and the coefficient of induction relating to these induced transient currents are denoted by M1, M2, M3, . . . The transient currents In1, In2, In3, . . . induced by the change in the magnetic flux density B are considered to be mutually independent. Here, the transient currents In1, In2, In3, . . . can be substituted by a single transient current i2 induced by a coefficient of induction M=ΣMi (i=1, 2, 3, . . . ) in accordance with the change in magnetic flux density B. Therefore, the course of disappearance of the magnetic flux Φ passing through any one sensor coil 4, can be expressed by the magnetic flux density B, and the transient current i2 induced by the coefficient of induction M, due to the change in magnetic flux density B.

FIG. 4 shows an equivalent circuit of FIG. 3. Here, R2 shows the electrical resistance relating to the transient current i2, and L2 shows the inductance relating to the transient current i2.

FIG. 5 is a diagram wherein the closed loop of magnetic flux Φ in the circuit diagram in FIG. 4 (the closed loop C2 passing through a single sensor coil 4 in FIG. 2) is substituted by an equivalent magnetic circuit. Here, i1 corresponds to the magnetic flux density (B in FIG. 4). R1 corresponds to a given irreversibility of the magnetic flux Φ. L1 corresponds to the inductance of the magnetic circuit, which is a physical quantity directly proportional to the volume of the whole magnetic flux space maintaining the magnetic flux Φ. Moreover, in the circuit diagram shown in FIG. 5, the coefficient of induction M corresponds to the mutual inductance between the inductance L1 of the magnetic circuit and the inductance L2 of the transient current circuit.

FIG. 6 shows a schematic view of the closed loop C2 having magnetic flux Φ (magnetic flux density B (=i1)) passing through a single sensor coil 4, after the static magnetic field F1 has been shut off. As described previously, after shut off of the static magnetic field, the magnetic energy W accumulated in the steel plate member 110 during the application of the magnetic field declines gradually, rather than disappearing immediately. This magnetic energy W is maintained in the closed loop space of magnetic flux Φ, and it gradually disappears in accordance with the irreversibility R1 of the magnetic flux Φ. In general, the magnetic energy W can be expressed by the following equation (1).

$$W = \frac{1}{2\mu} \int i_1^2 dv = \frac{1}{2} L i_1^2 \qquad (1)$$

Here, L is a value that is directly proportional to the volume of the space in which a magnetic flux of magnetic flux density i1 is maintained, in other words, the volume of the space in which the magnetic energy is maintained. On the other hand, Equation (1) is the same as the equation expressing the energy accumulated when a current of i1 flows in a coil of inductance L. Therefore, it can be seen that the inductance L1 in the circuit diagram shown in FIG. 5 is directly proportional to the volume of the total space in which the magnetic flux is maintained.

The equivalent circuit shown in FIG. 5 can be represented by Equation (2).

$$\left. \begin{array}{l} L_1 \dfrac{di_1}{dt} + R_1 i_1 - M \dfrac{di_2}{dt} = 0 \\ L_2 \dfrac{di_2}{dt} + R_2 i_2 - M \dfrac{di_1}{dt} = 0 \end{array} \right\} \qquad (2)$$

If the simultaneous differential equations indicated in Equation (2) are solved for i1 and i2, then the following equations (3a) and (3b) are obtained as respective solutions.

$$i_1 = A_1 \exp\{-(\alpha - \gamma)t\} - A_2 \exp\{-(\alpha + \gamma)t\} \qquad (3a)$$

$$i_2 = A_3 \exp\{-(\alpha - \gamma)t\} - A_4 \exp\{-(\alpha + \gamma)t\} \qquad (3b)$$

$$\alpha = \frac{L_1 R_2 + L_2 R_1}{2(L_1 L_2 - M^2)}$$

$$\gamma = \frac{\sqrt{(L_1 R_2 - L_2 R_1)^2 - 4R_1 R_2 M^2}}{2(L_1 L_2 - M^2)}$$

$$A_1 = \frac{-(L_1 R_2 - L_2 R_1) - \sqrt{(L_1 R_2 - L_2 R_1)^2 + 4R_1 R_2 M^2}}{2R_1 \sqrt{(L_1 R_2 - L_2 R_1)^2 + 4R_1 R_2 M^2}}$$

$$A_2 = \frac{(L_1 R_2 - L_2 R_1) - \sqrt{(L_1 R_2 - L_2 R_1)^2 + 4R_1 R_2 M^2}}{2R_1 \sqrt{(L_1 R_2 - L_2 R_1)^2 + 4R_1 R_2 M^2}}$$

$$A_3 = \frac{-M}{\sqrt{(L_1 R_2 - L_2 R_1)^2 + 4R_1 R_2 M^2}}$$

$$A_4 = A_3$$

Here, the respective constants in equation (3a) and equation (3b) are determined for the initial conditions, wherein the magnetic flux density i1 (=B) is taken to be B0 at the time that the static magnetic field F1 is shut off (t=0). In this case, assuming that the coefficient of induction M is low and the transient current i2 induced by change in the magnetic flux density i1 is very small, in other words, $L_1 \cdot L_2 \gg M \cdot M$, then the following results are obtained.

$$\alpha - \gamma \approx \frac{R_1}{L_1} = \frac{1}{\tau_1} \qquad (4a)$$

$$\alpha + \gamma \approx \frac{R_2}{L_2} = \frac{1}{\tau_2} \qquad (4b)$$

$$A_1 \approx I_0 \approx -\frac{1}{R_1} \qquad (4c)$$

$$A_2 \approx 0 \qquad (4d)$$

$$A_3 \approx 0 \qquad (4e)$$

$$A_4 \approx 0 \qquad (4f)$$

If Equation (4a) and Equation (4b) are substituted into Equation (3a), and i1 is substituted for B, then equation (5) is obtained.

$$B = A_1 \exp(-t/\tau_1) - A_2 \exp(-t/\tau_2) \qquad (5)$$

Equation (5) indicates the transient change in the magnetic flux density B of the magnetic flux Φ passing through the sensor coil 4. Here, taking Equation (4d) into account, it is possible to ignore the second item on the right-hand side of Equation (5). Therefore, the change in the magnetic flux density B of the magnetic flux Φ forming the closed loop C2 shown in FIG. 6 can be approximated to the first item on the right-hand side of Equation (5) only. FIG. 7a indicates the transient change in the magnetic flux density B given by the first item on the right-hand side of Equation (5) only, after the time at which the magnetic field is shut off (t=0). The value of the magnetic flux density before t=0 indicates the magnetic flux density B0 when the static magnetic field is being applied. On the other hand, the transient voltage actually detected by a sensor coil 4 during the course of disappearance of the magnetic field is equal to the rate of change of the magnetic flux density B with respect to time, in other words, the differential magnetic flux density dB/dt, multiplied by the cross-sectional area of the magnetic flux passing through the sensor coil 4. Therefore, by differentiating both sides of Equation (5) with respect to time t, Equation (6), in other words, an equation for the differential magnetic flux density, can be derived.

$$\frac{dB}{dt} = -\frac{A_1}{\tau_1}\exp(-t/\tau_1) + \frac{A_2}{\tau_2}\exp(-t/\tau_2) \quad (6)$$

$$= -\frac{A_1}{\tau_1}\left\{\exp(-t/\tau_1) - \frac{A_2\tau_1}{A_1\tau_2}\exp(-t/\tau_2)\right\}$$

$$= -\frac{A_1}{\tau_1}\{\exp(-t/\tau_1) - \exp(-t/\tau_2)\}\left(\because t=0, \frac{dB}{dt}=0 \rightarrow \frac{A_2\tau_1}{A_1\tau_2}=1\right)$$

$$= -\frac{B_0}{\tau_1}\{\exp(-t/\tau_1) - \exp(-t/\tau_2)\}(\because A_1 \approx B_0)$$

$$= -\frac{B_0}{\tau_1}\exp(-t/\tau_1) + \frac{B_0}{\tau_1}\exp(-t/\tau_2)(= f_1(t) + f_2(t))$$

FIG. 7b shows the transient change in the differential magnetic flux density obtained by Equation (6). This waveform is known to coincide approximately with the waveform obtained when actual measurements are taken used a sensor coil 4 as a magnetic sensor. Therefore, it can be maintained that the model described with respect to FIG. 3 to FIG. 6 is an accurate reflection of the course of disappearance of the residual magnetic field. In other words, Equation (5) represents the change in the magnetic flux density B of the magnetic flux Φ passing through the sensor coil 4, and Equation (6) represents the differential change of the magnetic flux density dB/dt.

Here, it can be seen that term $\tau_1$ in the first item on the right-hand side of Equation (6) is equal to L1/R1, as can be deduced from Equation (4a), and therefore it is equivalent to the time constant of the magnetic circuit of magnetic flux density i1 (=B) shown in FIG. 5. Consequently, the first item on the right-hand side of Equation (6) represents ideal steady attenuation characteristics wherein the magnetic flux density B of the magnetic flux in the vicinity of the steel plate member 110 declines exponentially after the static magnetic field F1 has been shut off, in other words, it represents the ideal attenuation characteristics of the magnetic energy. Here, it is supposed that the time constant $\tau_1$ contained in the first item on the right-hand side of Equation (6) is called the "main time constant". FIG. 7c shows the attenuation characteristics of the magnetic energy expressed by the first item on the right-hand side of Equation (6) (the closed loop C2 of the magnetic flux Φ).

In order to determine the main time constant $\tau_1$, firstly, Equation (7) is obtained by taking the logarithm of either side of f1(t) expressed by the first item on the right-hand side of Equation (6). If Equation (7) is plotted on a graph, a straight line of gradient $1/\tau_1$ is obtained. Therefore $\tau_1$ can be determined from the gradient of the graph.

$$\ln f_1(t) = -\ln\frac{B_0}{\tau_1} + \frac{t}{\tau_1} \quad (7)$$

In the manner described above, it is possible to determine the main time constant of the transient change in the differential magnetic flux density of the residual magnetic field which disappears after the static magnetic field has been shut off.

The second term $\tau_2$ in the right-hand side of Equation (6) is equal to $L_2/R_2$ as will be understood from Equation (4b), and thus corresponds to the time constant of the equivalent circuit of the eddy current $i_2$ in FIG. 5. Therefore, the second term in the right-hand side of Equation (6) expresses the damping characteristic of eddy current loss. FIG. 7d shows the damping characteristic of the eddy current loss represented by the second term of the right-hand side in Equation (6). Hereafter, the time constant $\tau_2$ of the second term of the right-hand side of Equation (6) will be called the secondary time constant. The secondary time constant $\tau_2$ can be obtained in the same way as described for $\tau_1$.

The main time constant $\tau_1$ obtained as described is proportional to $L_1$. On the other hand, $L_1$ is proportional to the magnetic permeability μ of the magnetic path through which the magnetic flux Φ passes. These facts show that the main time constant $\tau_1$ is proportional to the magnetic permeability μ. It should also be noted that the nugget section 102, the pressure bonded section 103 and the HAZ 104 of the spot weld section have different metallographic structures and therefore different magnetic permeabilities μ. Specifically, it is known that the magnetic permeability μ decreases as the hardness increases.

The non-destructive inspection method disclosed in the Japanese Patent Application Laid-Open No. 10-26209 uses the measuring principles described above in obtaining the main time constant $\tau_1$ of the magnetic energy damping characteristic at each location of the sensor coils 4, and uses the distribution of the main time constant $\tau_1$ as the basis of estimation of the nugget diameter L2 of the nugget section 102 which is the hardest in the spot weld section and therefore has the lowest magnetic permeability μ.

Specifically, first, as shown in FIG. 8a, a row of e.g. sixteen sensor coils 4 are arranged to face the spot weld section and its surroundings for measurement of the damping characteristic of the magnetic flux Φ in the residual magnetic field by each of the sensor coils 4. From this measurement data, the main time constant $\tau_1$ is obtained for each of the sensor coils 4. As shown in FIG. 8b, the distribution of the $\tau_1$ for the respective sensor coils 4 can be expressed by a step function with the measurement position x as the variable. Next, as shown in FIG. 8c, an approximate curve f(x) (solid line) of the step function is calculated by the least squares method. Supposing that only the nugget section 102 has a relatively low magnetic permeability, and all the other regions have the same magnetic permeability, the recess in the approximate curve f(x) for the $\tau_1$ distribution reflects the existence and the geometry of the nugget section 102, for $\tau_1$ is proportional to the magnetic permeability. Thus, according to the technique disclosed in the JP Laid-Open No. 10-26209, the shape of the recess in the approximate curve f(x) for the $\tau_1$ distribution is used for estimating the nugget diameter L2 as shown in FIG. 8c.

As discussed earlier, the damping characteristic main time constant $\tau_1$ of the magnetic flux $\Phi$ through the sensor coil 4 is proportional to the inductance $L_1$, and $L_1$ is proportional to the magnetic permeability $\mu$. It is also known that $L_1$ is proportional to the volume V of the space through which the magnetic flux $\Phi$ passes. Thus, the relationship expressed in Equation (8) holds for the main time constant $\tau_1$:

$$\tau_1 \propto \mu V \tag{8}$$

As noted above, air has an extremely smaller magnetic permeability than any of the magnetic matters in the spot weld section. For this reason, the $\tau_1$ calculated for the measurement positions facing the indentations 101 in FIG. 18 is smaller than the counterpart values for other measurement positions, whether or not the nugget section 102 exists. In other words, the recess in the graph in FIG. 8c includes a component resulted from the indentations 101. If the spot weld section were flat with no indentations 101 formed, the $\tau_1$ distribution approximate curve f(x) should have a shallower recess as shown by the broken line in FIG. 8c. Thus, if the non-destructive inspection method of a spot weld section utilizes only one approximate curve f(x) of the distribution of $\tau_1$, it may be difficult to obtain an accurate estimation for the nugget diameter L2 due to the noise caused by the presence of the indentations 101.

BEST MODE FOR CARRYING OUT THE INVENTION

Figure 9:
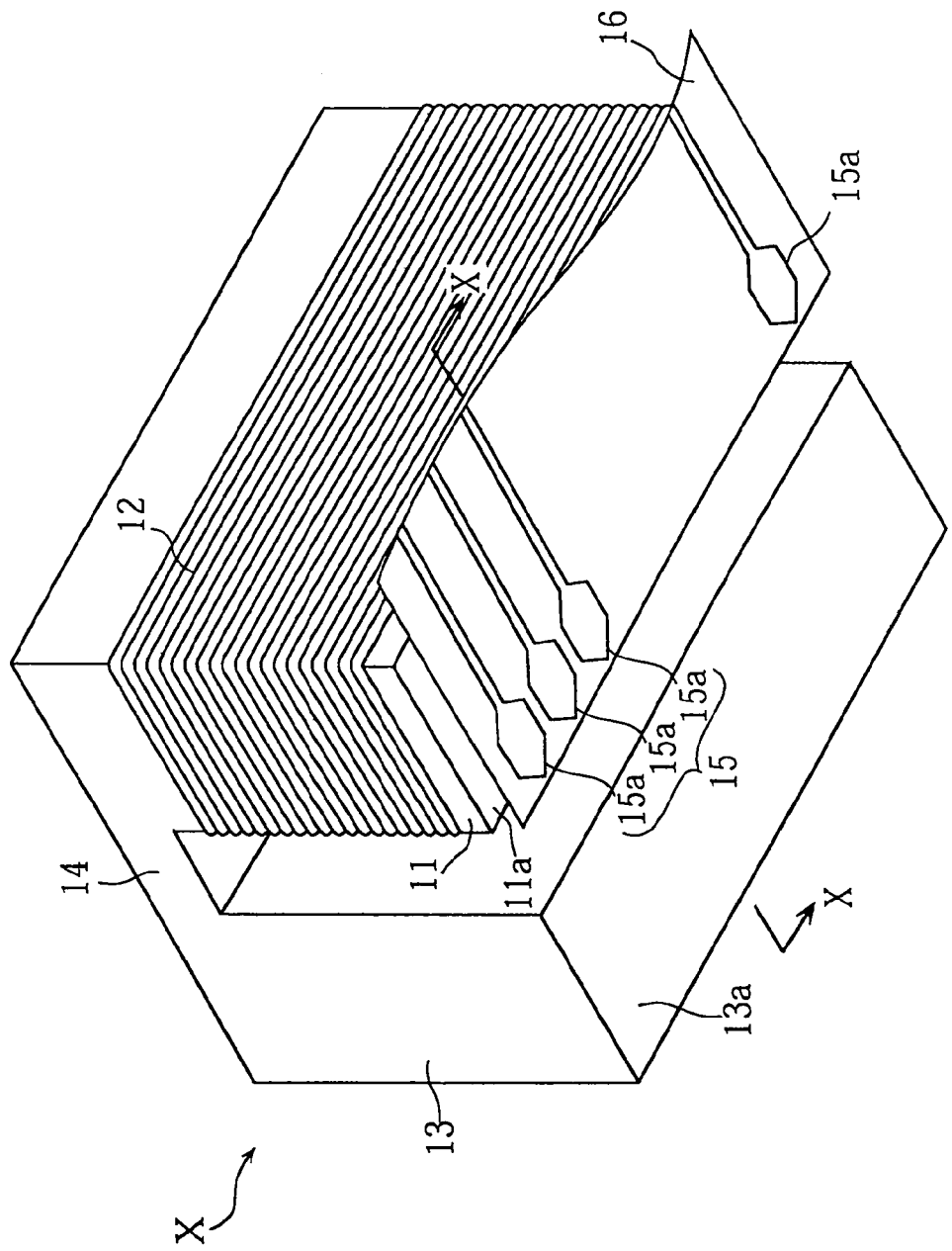
FIG. 9 shows a non-destructive inspection apparatus capable of carrying out a non-destructive inspection method according to the present invention.
Figure 10:
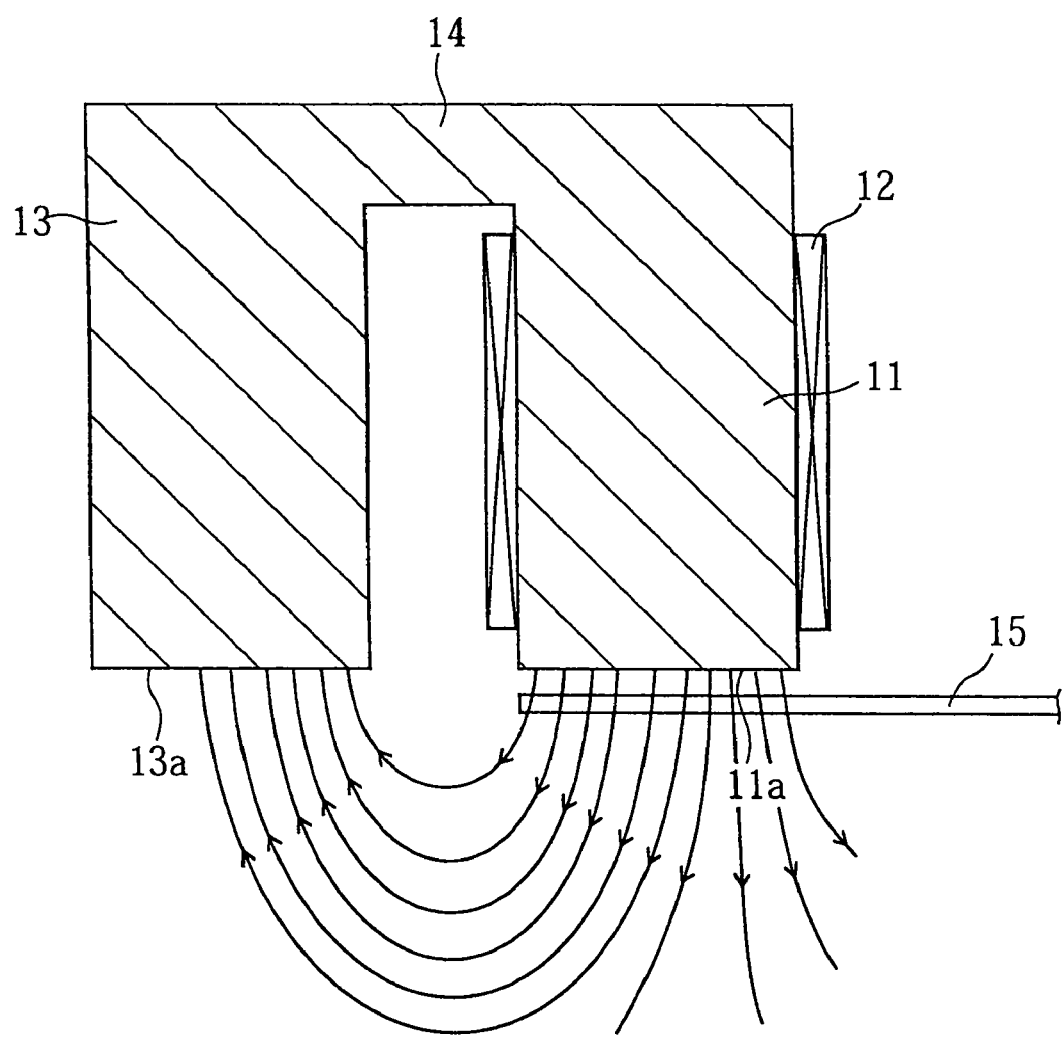
FIG. 10 is a sectional view taken in lines X—X in FIG. 9.

FIG. 9 shows a non-destructive inspection apparatus X for carrying out a non-destructive inspection method according to the present invention. FIG. 10 is a sectional view taken along lines X—X in FIG. 9, showing the state of the magnetostatic field formed. The non-destructive inspection apparatus X performs a non-destructive inspection based on the above-described measuring principles which involve the applying and shutting-off of the magnetostatic field. The non-destructive inspection apparatus X includes an exciting pole 11, an excitation coil 12 wound about the exciting pole, a recovering pole 13, a connecting portion 14 to connect the exciting pole 11 and the recovering pole 13, and a coil array 15 disposed in the vicinity of the exciting pole 11.

The exciting pole 11 is an iron core for increasing the magnetic flux density of the magnetic field which is induced by a current flowing through the excitation coil 12, and is integral with the recovering pole 13 via the connecting portion 14. The exciting pole 11 has a magnetic flux exciting surface 11a at its end. The recovering pole 13 has a recovering surface 13a at its end. Magnetic fluxes coming from the magnetic flux exciting surface 11a of the exciting pole 11 are recovered by the recovering surface 13a.

The coil array 15, provided by a row of loop coils 15a according to the present embodiment, detects magnetic changes near an inspection region during the application and after the shutoff of the magnetostatic field, and outputs the measured changes in the form of voltage. Each loop coil 15a is made of an electrically conductive material such as copper, and is patterned on a flexible substrate 16. As shown in FIG. 9, the coil array 15 is right beneath the magnetic flux exciting surface 11a, spaced from the magnetic flux exciting surface 11a by a predetermined distance, so that the row of loop coils 15a lies longitudinally of the magnetic flux exciting surface 11a. The coil array 15 is placed in such a relationship to the magnetic flux exciting surface 11a of the exciting pole 11 that the loop coils 15a are displaced toward the recovering pole 13. Such a construction makes it possible to efficiently measure the magnetic flux of the magnetostatic field headed toward the recovering surface 13a and measure the residual magnetic field generated when the magnetostatic field is shut off.

Figure 11:
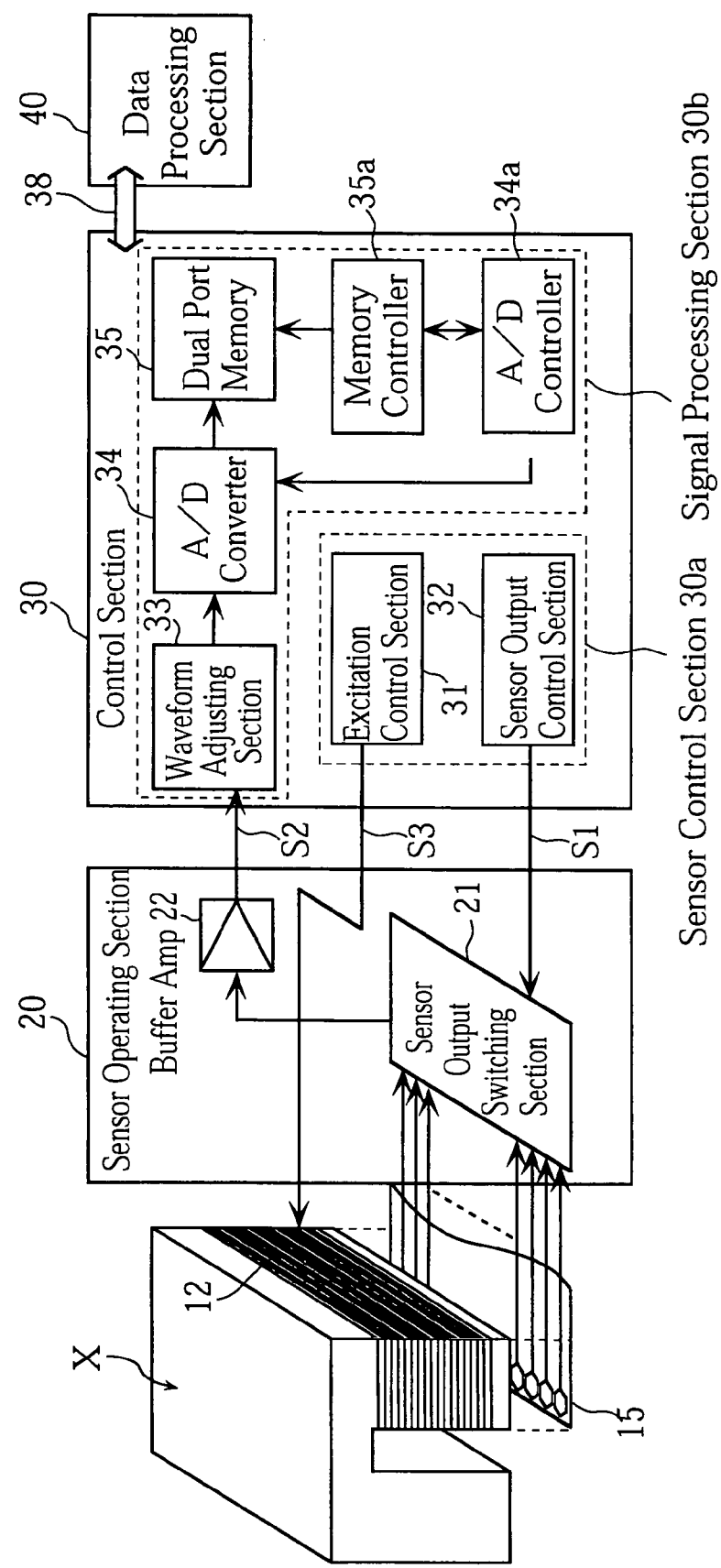
FIG. 11 shows a configuration of a system for operating the non-destructive inspection apparatus in FIG. 9.

FIG. 11 shows the composition of a system for operating the non-destructive inspection device X1. This system comprises a sensor operating section 20, a control section 30 and a data processing section 30.

The sensor operating section 20 comprises a sensor output switching section 21 and a buffer amp 22. The sensor output switching section 21 is a circuit for selecting only one output of the respective outputs of the plurality of loop coils 15a constituting the coil array 15, and outputting same to the buffer amp 22. The sensor output switching section 21 selects the outputs of the respective loop coils 15a, sequentially, and outputs same to the buffer amp 22, in accordance with a 4-bit sensor output switching signal S1. The buffer amp 22 is a buffer circuit for outputting the output signal from the sensor output switching section 21 to the control section 30, in the form of a detection signal S2.

The control section 30 is formed by a control circuit connected via a generic bus 38 to the data processing section 40, and it comprises a sensor control section 30a and a signal processing section 30b. The sensor control section 30a comprises an excitation control section 31 and a sensor output control section 32. The signal processing section 30b comprises a waveform adjusting section 33, an A/D converter 34, a dual port memory 35, an A/D controller 34a, and a memory controller 35a. The control section 30 is formed on a control substrate connected to a generic slot of a computer.

The excitation control section 31 of the sensor control section 30a outputs a drive signal S3 to the excitation coil 20, in order to generate or shut off a static magnetic field of a prescribed intensity. In other words, the excitation control section 31 applies and shuts off a prescribed voltage, to the excitation coil 12. The sensor output control section 32 outputs a 4-bit sensor output switching signal S1 for sequentially selecting the output from the plurality of loop coils 15a contained in the coil array 15, to the sensor output switching section 21.

The waveform adjusting section 33 of the signal processing section 30b adjusts the detection signal S2 from the buffer amp 22, in accordance with the input specification of the A/D converter 34. The A/D converter 34 converts the input detection signal from analog to digital. The dual port memory 35 stores the digital data after A/D conversion. The A/D controller 34a controls the timing of the A/D converter 34. The memory controller 35a controls the operations of writing to and reading from the dual port memory 35.

If the inspection target is a steel plate, then the effects of the eddy current loss appear notably in the transient change characteristics of the detection signal S2 after approximately 10 µs or less from the shut off of the static magnetic field (the average value being approximately 3 to 6 µs). Taking account of this fact, and the accuracy of data processing, it is desirable that the A/D converter 34 has a conversion speed of 4 Msps or above, and a conversion accuracy of 12 bits, or more.

The data processing section 40 is realized by means of a general computer having non-illustrated CPU and main memory. In the data processing section 40, the nugget diameter of the spot weld section is found by processing detection data which is output by the sensor operating section 20 and processed by the signal processing section 30b. The data processing section 40 comprises a monitor for displaying various measurement waveforms and measurement data tables. The various types of data processing described hereinafter are achieved by executing a computer program stored in a main memory (storage medium) by a CPU in the data processing section 40.

With the non-destructive inspection apparatus X and the operating system described above, it is possible to carry out a non-destructive inspection method according to the present invention.

Figure 12:
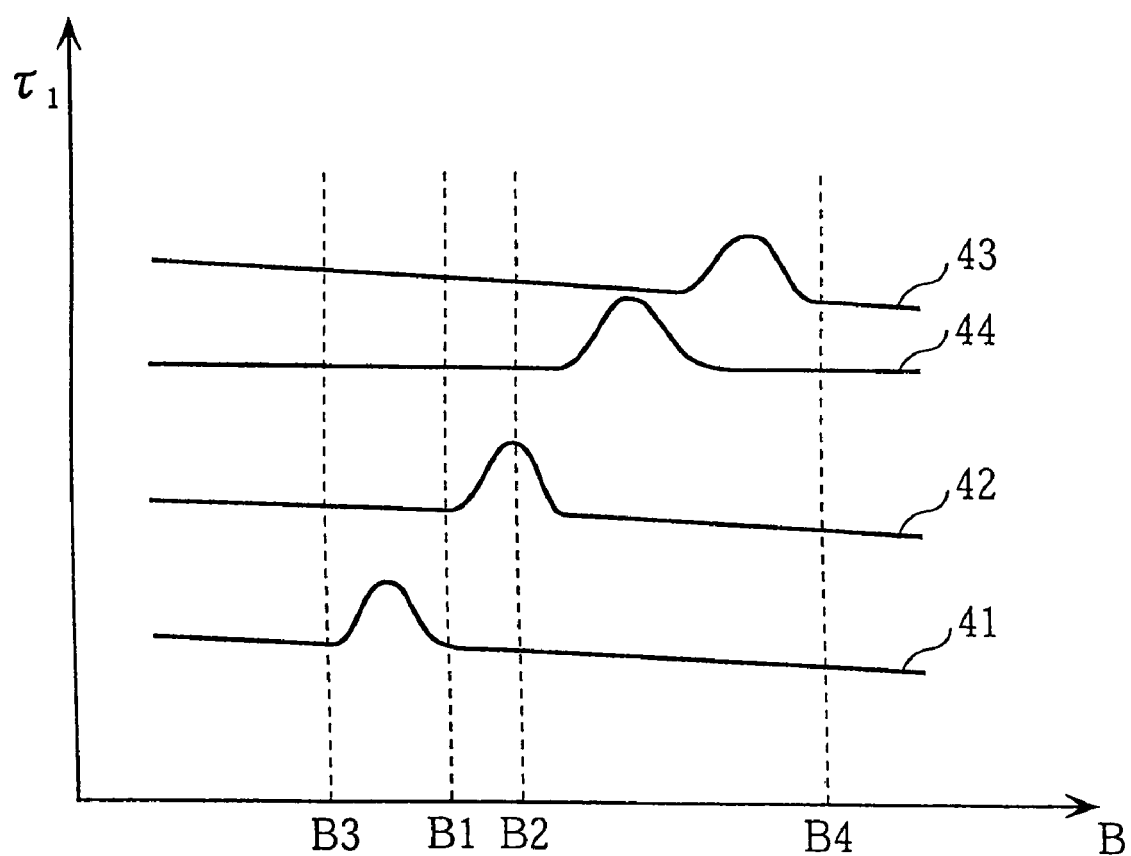
FIG. 12 show how a main time constant $\tau_1$ changes in different metallographic structures in a spot weld section, along with changes in magnetic flux density B of an applied magnetostatic field.
Figure 19:
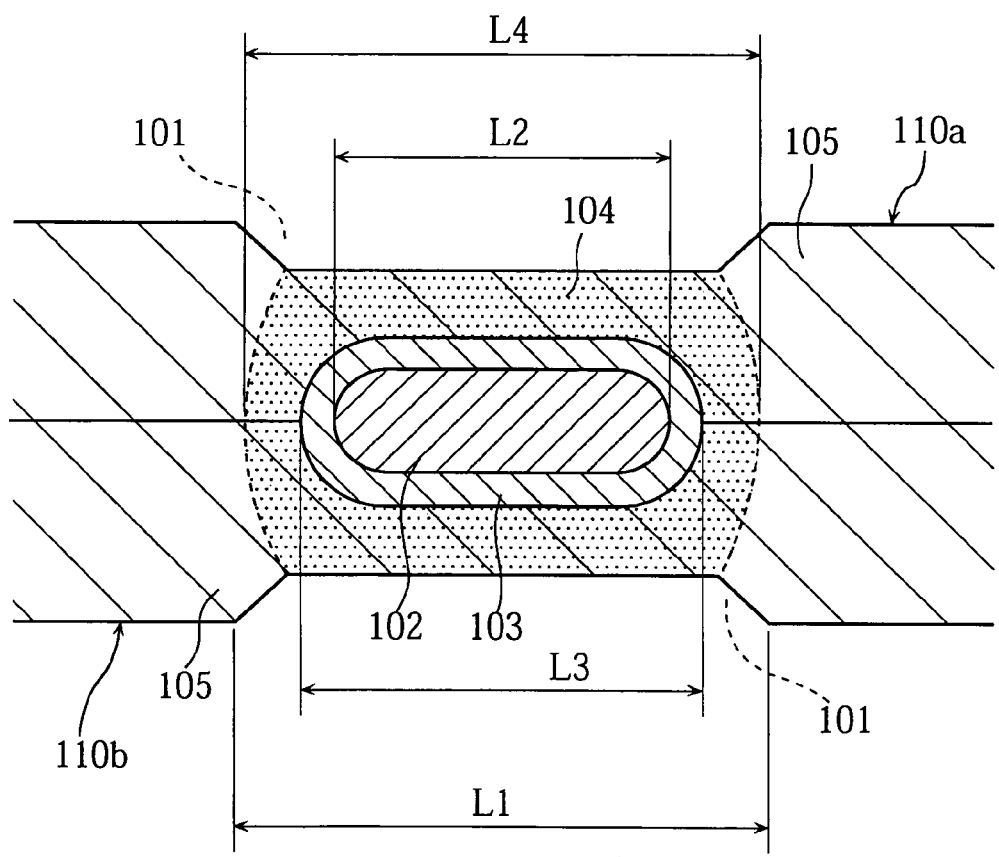
FIG. 19 is a sectional view of a spot weld section made by spot welding two sheet metals.

FIG. 12 shows how main time constants $\tau_1$ corresponding to different metallographic structures in a spot weld section will change as the magnetic flux density B of an applied magnetostatic field changes. The graph shown in FIG. 12, representing the changes of the main time constants $\tau_1$, is obtained by using the above-described measurement principles applied to individually-prepared metallic samples which are arranged to simulate, respectively, the nugget section 102, the pressure bonded section 103, the HAZ 104 and the original metal 105, which are disposed at or near the spot weld section shown in FIG. 19. The curves 41, 42, 43 and 44 correspond to the nugget section 102, the pressure bonded section 103, the HAZ 104 and the original metal 105, respectively.

As shown in FIG. 12, the main time constants $\tau_1$ tend to be greater for the nugget section 102, the pressure bonded section 103, the original metal 105 and the HAZ 104 in this order for the same magnetic flux density B. This is because, as noted above, the hardness of the nugget section 102, the pressure bonded section 103, the original metal 105 and the HAZ 104 becomes smaller in this order, while their magnetic permeability µ, which is proportional to the main time constant $\tau_1$, become greater along with the decrease in hardness. The main time constants $\tau_1$ for the respective sections are generally constant or show gentle linear changes; but in a relatively narrow range of the magnetic flux density, they increase fairly sharply, thereby providing a peak. When measurements are made under the same conditions, the peak of each curve appears at a given magnetic flux density B specific to the hardness of the section. Another tendency is that, in the illustrated range of the magnetic flux density, the specific value of the magnetic flux density B shifts toward the higher value side as the hardness becomes smaller.

The non-destructive inspection method according to the first embodiment of the present invention will be described with reference to FIG. 12 and FIG. 14 as well as the flowchart of FIG. 13. Specifically, in Step 1, the non-destructive inspection apparatus X is disposed so that a row of sixteen loop coils 15a serving as magnetic sensors are arranged to face the spot weld section and its surroundings. The locations of the loop coils 15a are represented by the measurement position x. Next, in Step S2, the non-destructive inspection apparatus X applies a magnetostatic field to the spot weld section, at a magnetic flux density B1. Preferably, referring to FIG. 12, the magnetic flux density B1 is greater than the magnetic flux density giving rise to the peak in the $\tau_1$ curve of the nugget section 102, but smaller than the magnetic flux density giving rise to the peak in the $\tau_1$ curve for the pressure bonded section 103. Next, in Step S3, the magnetostatic field is shut off. Next, in Step S4, the loop coils 15a measure the disappearance of the residual magnetic field for the spot weld section and its surroundings. Next, in Step S5, based on the measurements, the time constant $\tau_1$ at each measurement position is analyzed. Next, in Step S6, the values of the time constant $\tau_1$ for each sensor location, or measurement position x, are plotted, and than an approximate curve 61 as shown in FIG. 14b is calculated from the plot data by means of the least squares method. The approximate curve 61 may be displayed on the monitor of the data processing section 40, as necessary.

Figure 13:
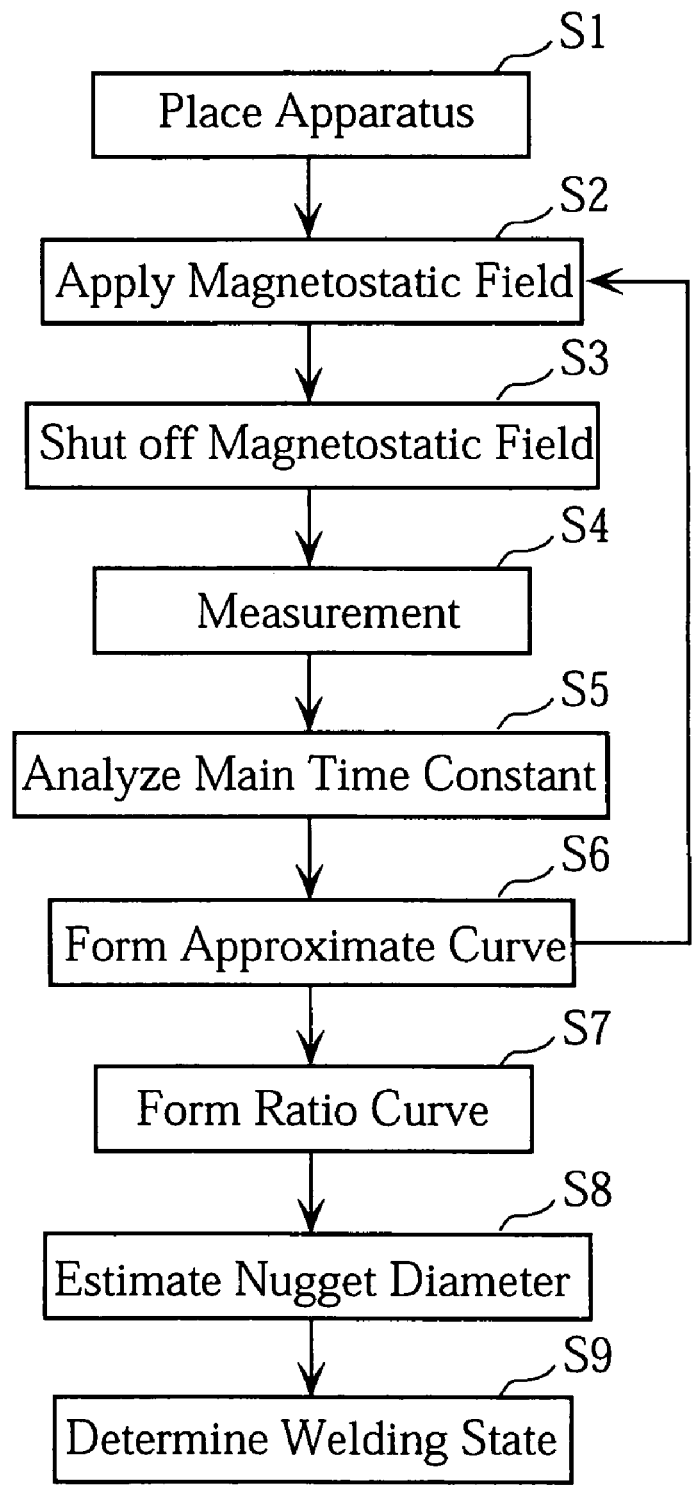
FIG. 13 is a flowchart of a first embodiment.
Figure 14A:
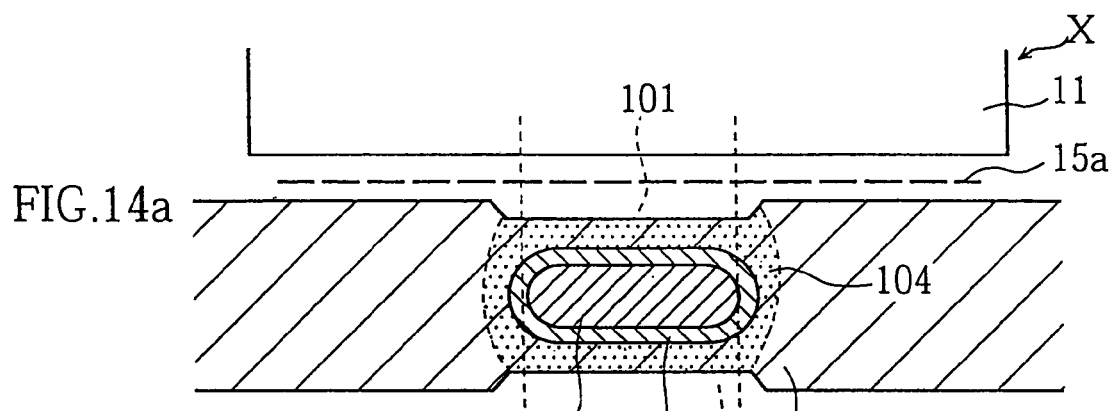
FIG. 14a through FIG. 14c illustrate a concept of non-destructive inspection method according to the first embodiment.
Figure 14B:
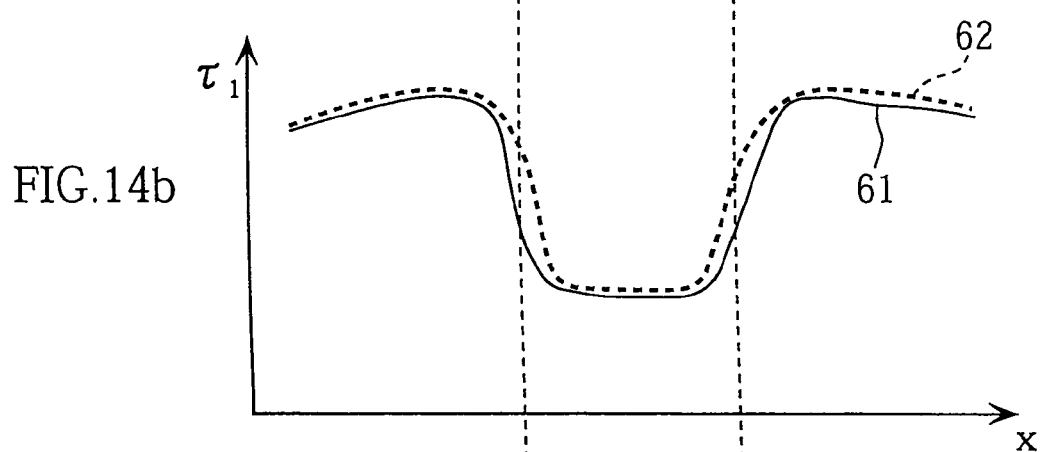

Next, the process goes back to Step S2 of the flowchart in FIG. 13, whereby the non-destructive inspection apparatus X, held at the initial position, applies a magnetostatic field again to the spot weld section and its surroundings, at a magnetic flux density of B2. As shown in FIG. 12, preferably the magnetic flux density B2 gives rise to the peak in the curve for the pressure bonded section 103, but not in any other curves for the other sections. Next, in Step S3, the magnetostatic field is shut off. In Step S4, the respective loop coils 15a measure the disappearance of the residual magnetic field for the spot weld section and its surroundings. Based on the measurements, in Step S5, the main time constants $\tau_1$ at each measurement position are analyzed. In Step S6, the main time constants $\tau_1$ for the respective sensor locations or measurement position x are plotted. From the plot data, an approximate curve 62 as shown in FIG. 14b is calculated by the least squares method. The approximate curve 62 may be displayed on the monitor of the data processing section 40, as necessary.

Each of the magnetic paths corresponding to the positions of the respective loop coils 15a, i.e., the measurement positions, extends through various portions constituting the spot weld section. As understood from FIG. 12, the time constant $\tau_1$ measured at each measurement position with the magnetic flux density B1 will be the same as the time constant $\tau_1$ measured at each measurement position with the magnetic flux density B2 if the magnetic paths corresponding to the respective measurement positions do not pass through the pressure bonded section 103. On the other hand, if most part of the magnetic path extends through the pressure bonded section 103, the time constant is greater when measured by the magnetic flux density B2 than when measured by the magnetic flux density B1. This difference is reflected in the occurrence of the peaks in the ratio curve 63 shown in FIG. 14c. In each of the approximate curves 61, 62 in FIG. 14b, a recess includes a component originated from the indentations 101, but the ratio curve 63 in FIG. 14c, which shows changes in the ratio between the two curves, does not includes the component from the indentations 101. Therefore, the present embodiment makes it possible to obtain information about the internal structure appropriately regardless of the outside surface undulation in the spot weld section.

Figure 14C:
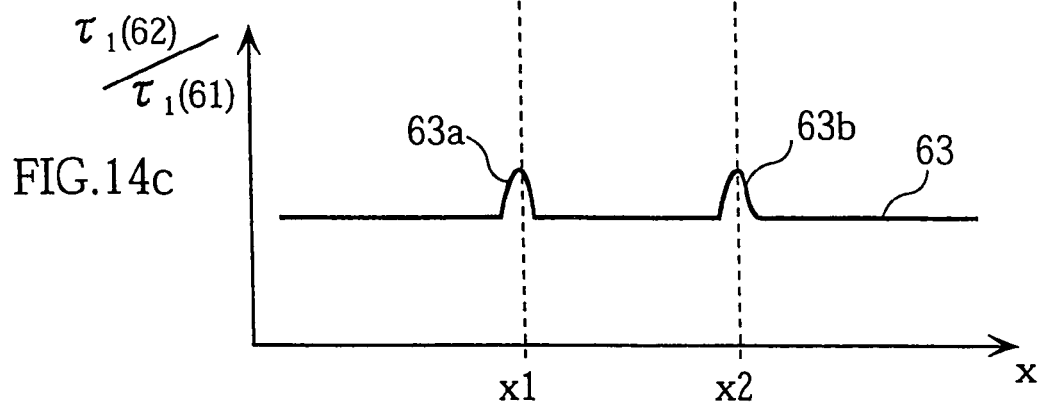
Figure 15:
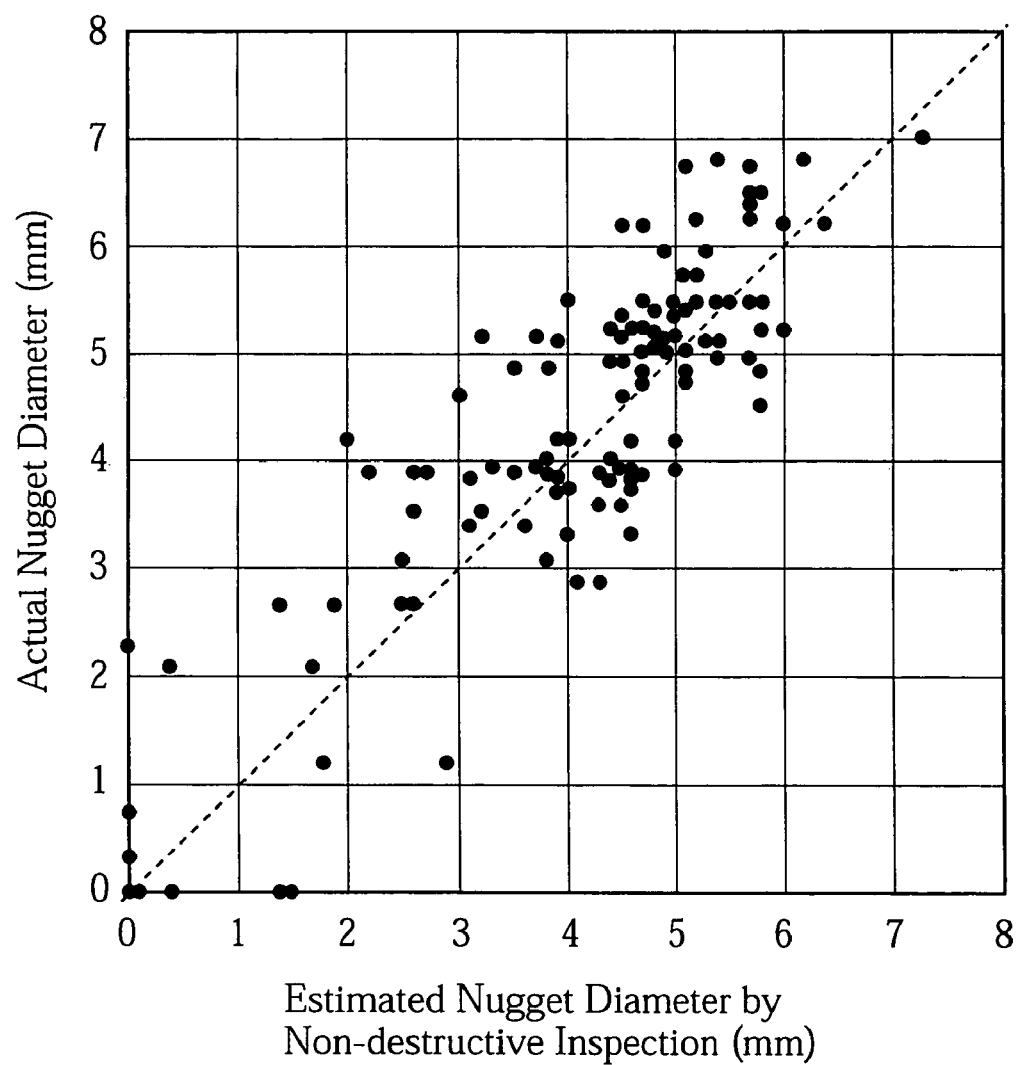
FIG. 15 shows an example of correlation data obtained by the present invention.

FIG. 14c shows a case in which the nugget diameter L2 is estimated to be the distance between the two peaks of the ratio curve 63. As to interpretation of a specific point in the peak to be the border between the nugget section 102 and the pressure bonded section 103, it is preferable that the interpretation should be made through a predetermined set of steps, on the basis of correlation data between the estimated nugget diameter L2 obtained from the peak data of the ratio curve 63 according to the present embodiment and actual measurement data of the nugget diameter L2.

Figure 16:
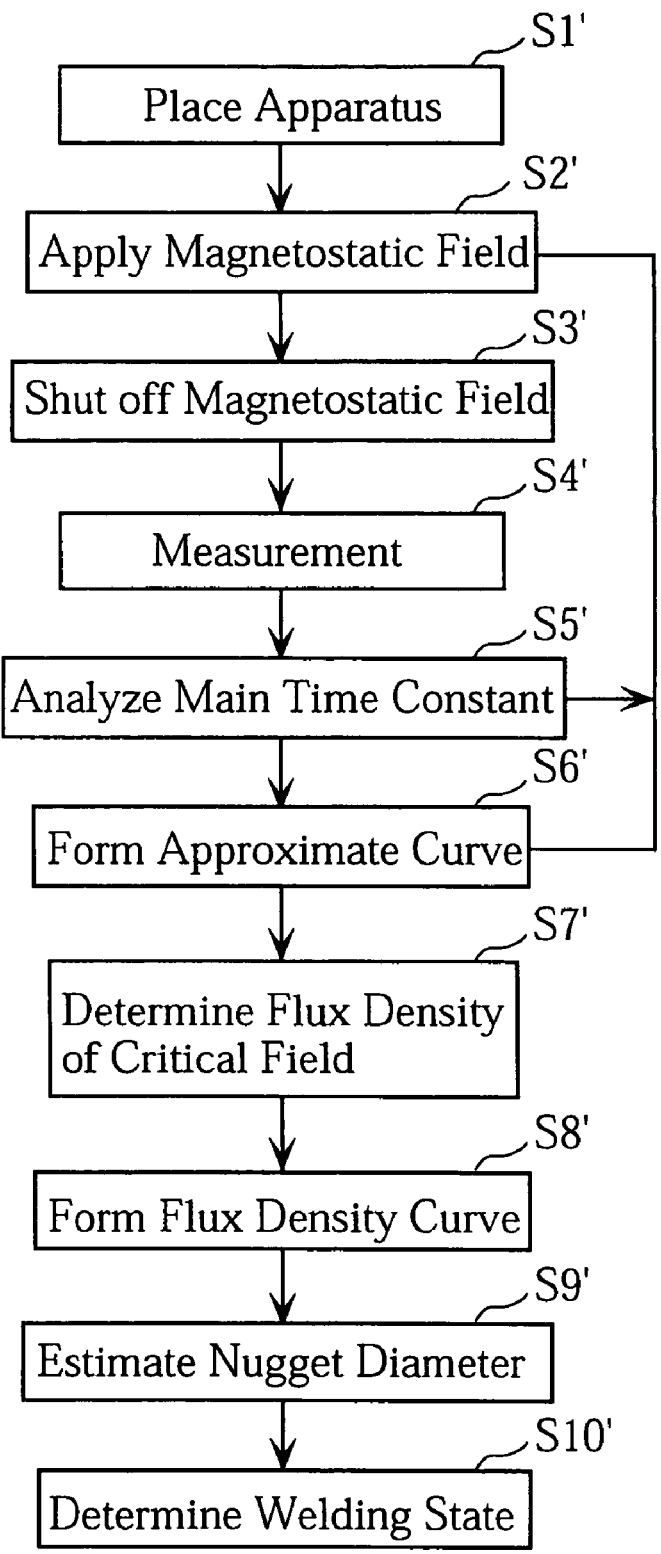
FIG. 16 is a flowchart of a second embodiment.

FIG. 16 shows a correlation data between estimated values of the nugget diameter L2 given by the peak-to-peak distance in the ratio curve 63 and values obtained from actual measurements of the nugget diameter L2. The correlation data yields a correlation coefficient of about 0.92, indicating that the estimated values are highly accurate.

According to the present embodiment, it is also possible to obtain other information such as diameters of other zones, by selecting two appropriate values based on the $\tau_1$ change curve data as shown in FIG. 12 for the magnetic flux density B of the applied magnetostatic field.

Figure 1:
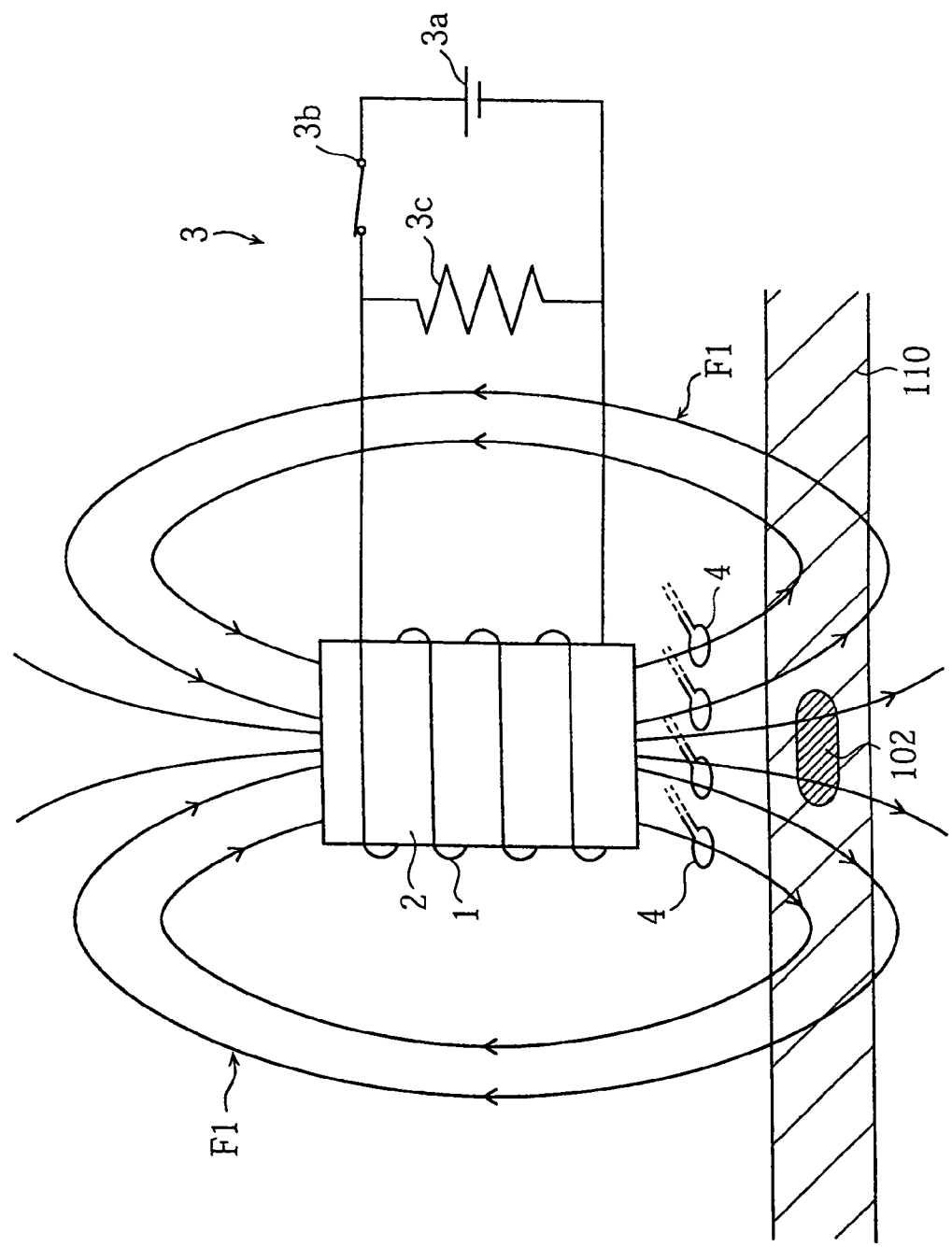
FIG. 1 is a schematic view outlining a constitution and operation of an apparatus for carrying out a non-destructive inspection through turning on and shutting off a magnetostatic field.
Figure 2:
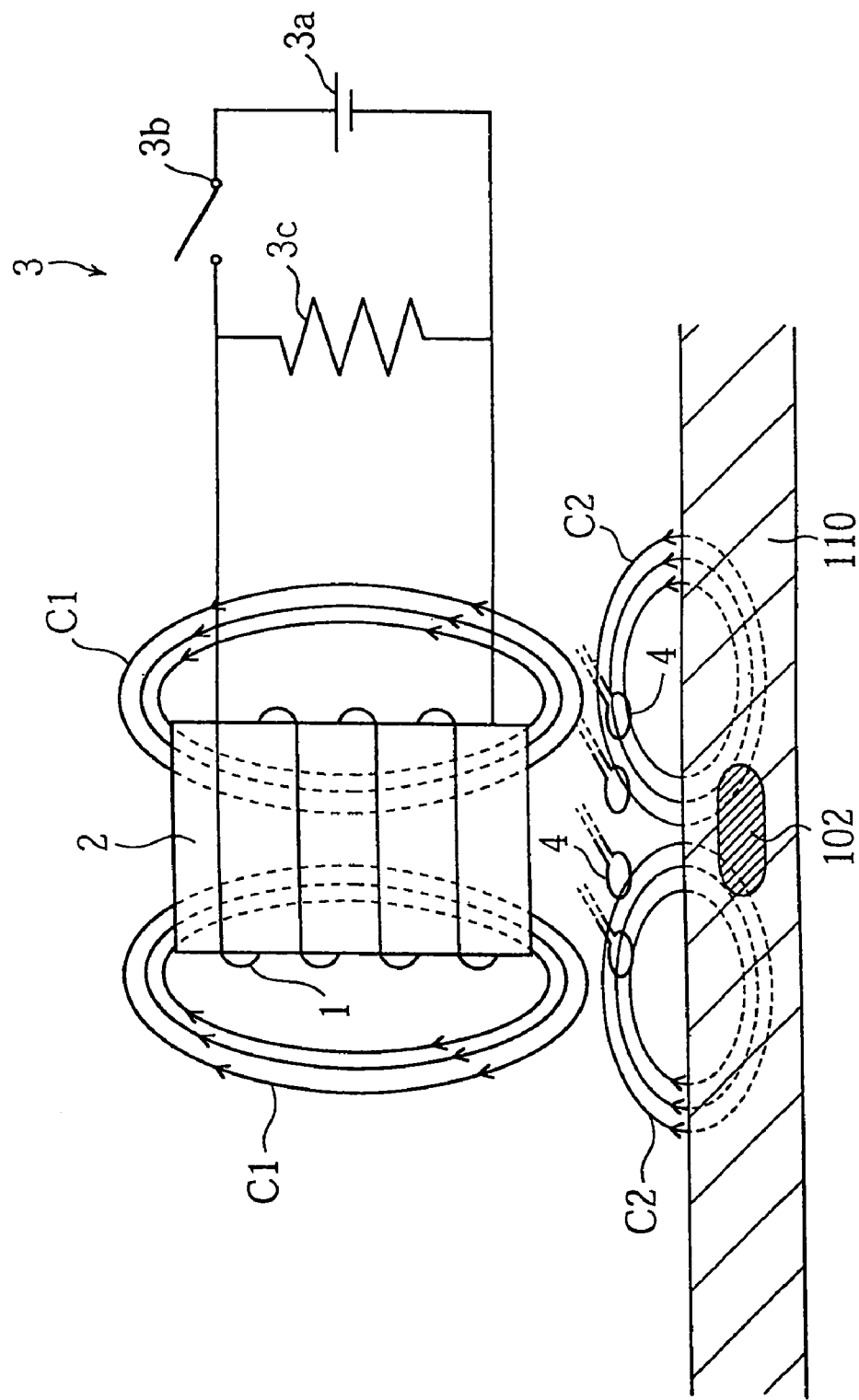
FIG. 2 is a schematic view outlining another constitution and operation of an apparatus for carrying out a non-destructive inspection through turning on and shutting off a magnetostatic field.
Figure 3:
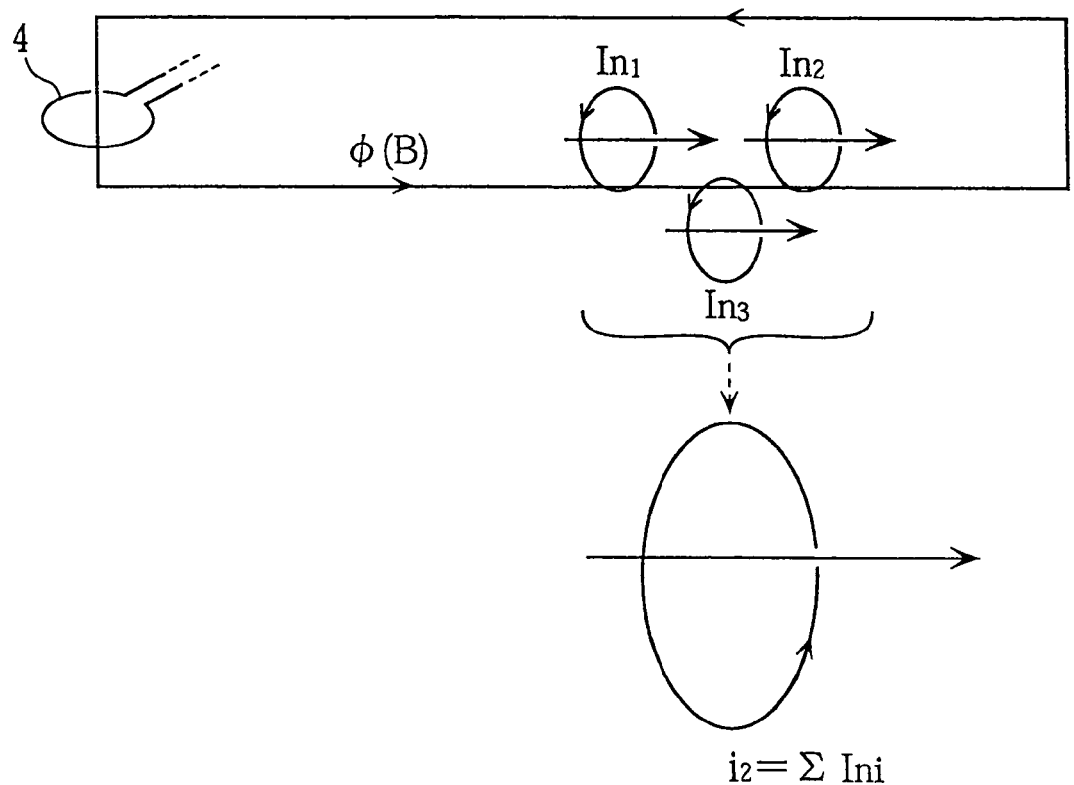
FIG. 3 shows a model of fading process of magnetic flux closed loops after a magnetostatic field is shut off.
Figure 4:
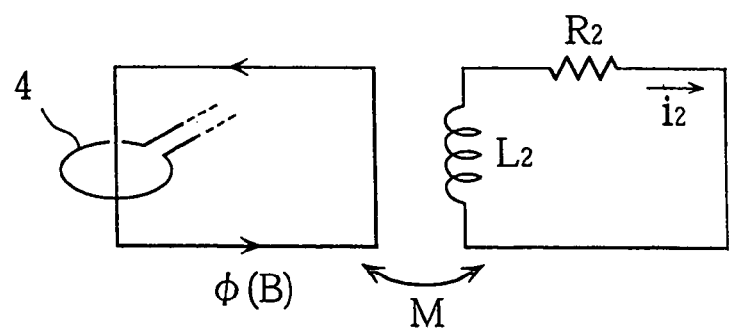
FIG. 4 shows an equivalent circuit of an eddy current shown in FIG. 3.
Figure 5:
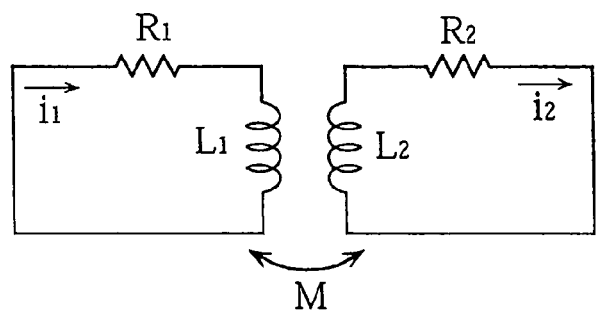
FIG. 5 shows an equivalent to FIG. 4, with a close loop of magnetic flux density replaced by a magnetically equivalent circuit.
Figure 6:
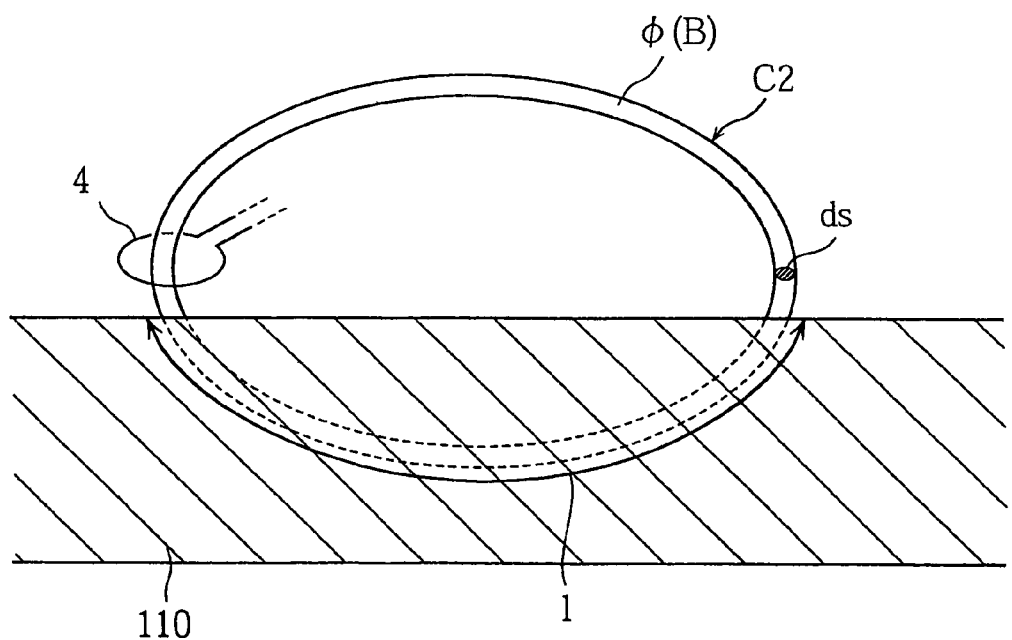
FIG. 6 shows a magnetic flux closed loop passing through a coil right after a magnetostatic field is shut off.
Figure 7A:
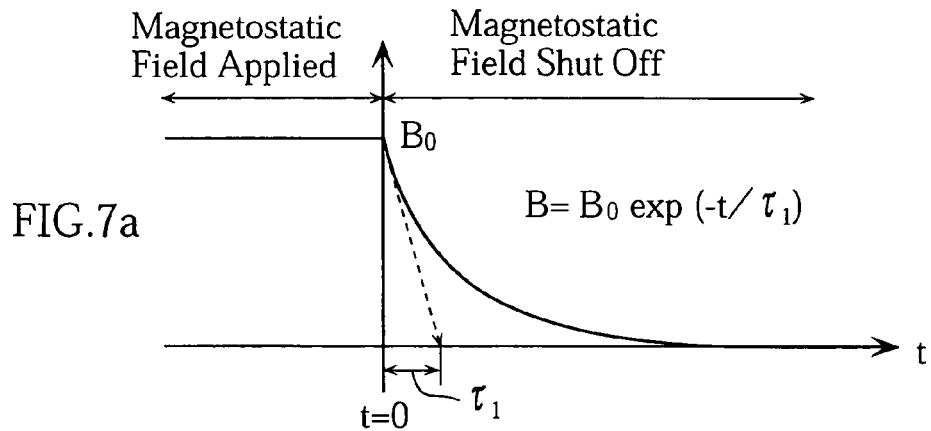
FIG. 7a through FIG. 7d show transient changes of different physical quantities in non-destructive inspection according to the present invention.
Figure 7B:
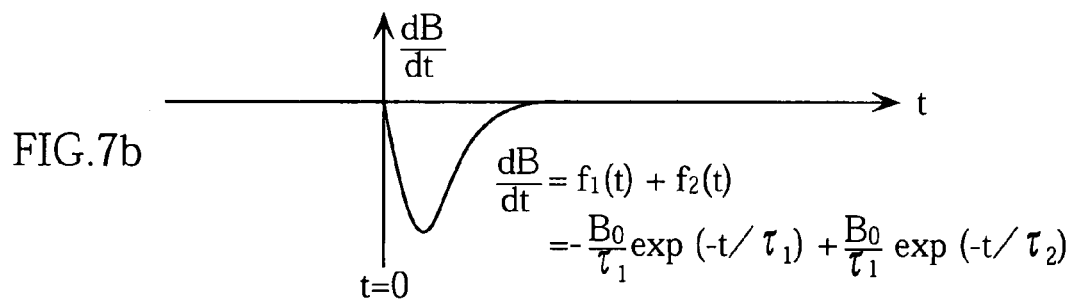
Figure 7C:
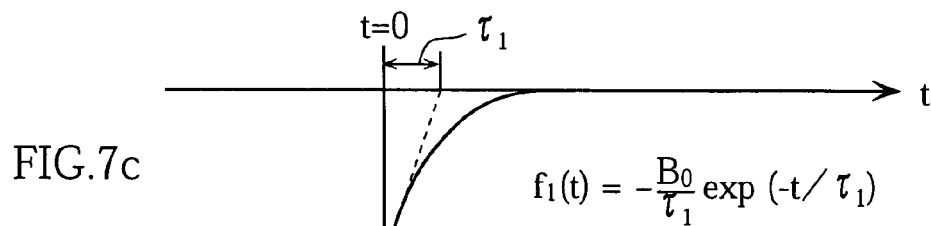
Figure 7D:
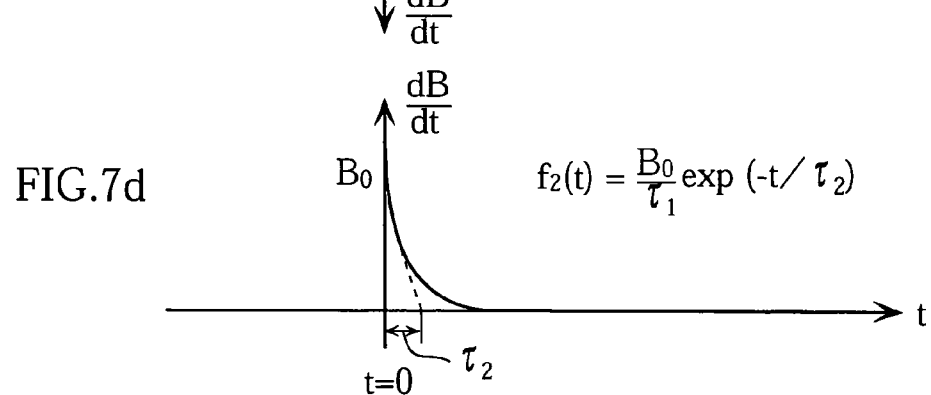
Figure 8A:
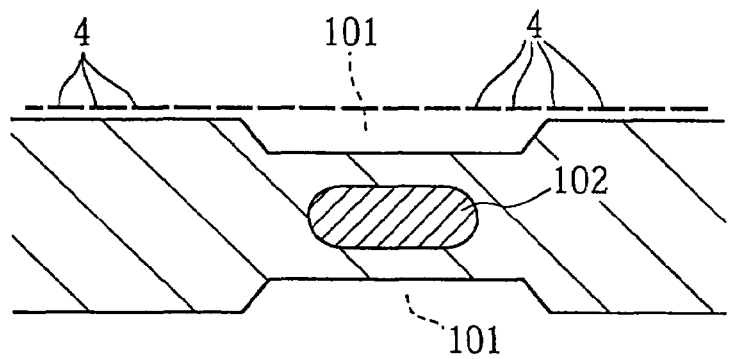
FIG. 8a through FIG. 8c illustrate a concept of an example method of measuring a nugget diameter.
Figure 8B:
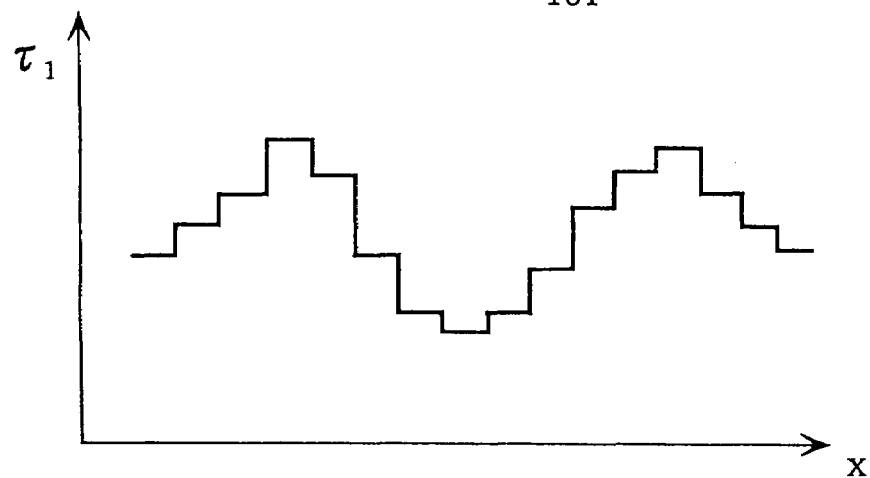
Figure 8C:
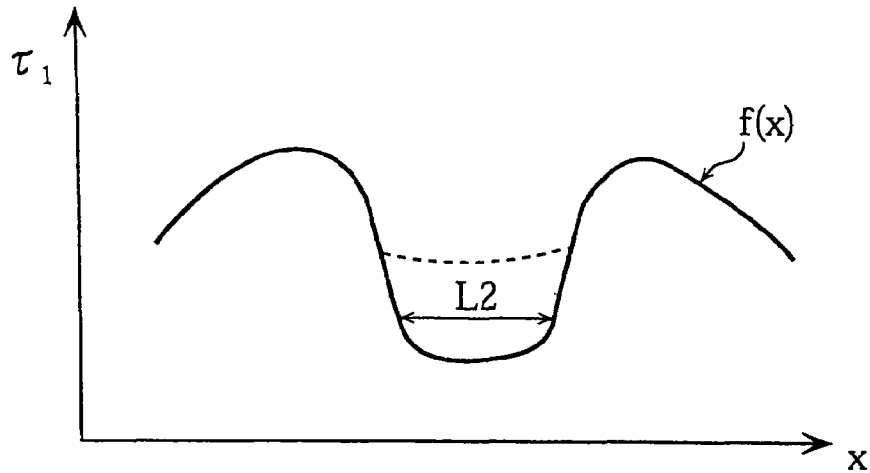

Next, a second embodiment of the present invention will be described with reference to FIG. 12, FIGS. 17a–17c and the flowchart in FIG. 16. First, in Step 1', as shown in FIG. 17a, the non-destructive inspection apparatus X is placed so that the row of sixteen loop coils 15a serving as magnetic sensors are arranged to face a spot weld section and its surroundings. The locations of the loop coils 15a are represented by measurement positions x. Next, in Step S2', the non-destructive inspection apparatus X applies a magnetostatic field to the spot weld section, at a magnetic flux density B3. As shown in FIG. 12, the magnetic flux density B3 ideally has a value smaller than a magnetic flux density which brings the time constant to the peak in the curve for the nugget section 102, but not in any other curves for the other regions. Next, in Step S3', the magnetostatic field is shut off. Next, in Step S4', measurements are made by each loop coil 15a for a fading process of a residual magnetic field at the spot weld section and its surroundings. Next, in Step S5', analyses are made for the time constant at each position of measurement, based on this particular cycle of measurements. In this step, analytical calculation is also made for a value of the magnetic flux density at t=0 which gave this particular set of main time constants. Specifically, the value is obtained by the data processing section 40 through an integrating operation from t=0 to t=∞ of the first term in the right-hand side of Equation (6) that corresponds to FIG. 7c. The main time constants and the corresponding magnetic flux densities B are stored in the main memory in the data processing section 40. Next, in Step S6', plotting is made for values of the time constant for each sensor location or measurement position x, and from the plot data is obtained an approximate curve 80 as shown in FIG. 17b by means of the least squares method. The approximate curve 80 is displayed on the monitor of the data processing section 40, as necessary. Step S6' may be skipped according to the present embodiment. It should be noted that the approximate curve 80 in FIG. 17b is schematic for simplicity of the drawing.

Next, the process goes back from Step S5' or S6' to Step S2' of the flowchart in FIG. 16, and a cycle of steps from Step S2' through Step S5' or S6 is repeated for n times, with the magnetic flux density B of the magnetostatic field applied by the non-destructive inspection apparatus X incremented by ΔB for each cycle. A value of the magnetic flux density in the n-th cycle is B4. As shown in FIG. 12, the magnetic flux density B4 is ideally greater than a magnetic flux density which brings the time constant to the peak in the curve for the HAZ 104, but not in the curves for any other zones. As described, according to the present embodiment, the magnetic flux density B of the applied magnetostatic field is varied, or changed for scanning, whereby changes in the main time constant at each measurement position is scanned.

After the scanning is finished, in Step S7', reference is made to the main memory in the data processing section 40, to identify for each measurement position a magnetic flux density value of a critical magnetostatic field where the time constant showed dramatic increase in response to the change in the magnetic flux density B. As will be understood from FIG. 12, each of the regions constituting the spot weld section and its surroundings has a specific magnetic flux density value for the critical magnetostatic field where the time constant shows dramatic increase, in a range between the magnetic flux density B3 at the beginning of scanning and the magnetic flux density B4 at the end of the scanning. At each position where one of the loop coils 15a is located, i.e. at each position of the magnetic path represented by one of the measurement positions, there is a complex of different zones that constitute the spot weld section. The variation in the main time constant at each measurement position is a significant representation of an influence by the structure (zone) which takes a primary or the largest volume at this particular position of the magnetic path. FIG. 17b gives a schematic view of different waveforms (approximate curves) of the main time constant at each magnetic flux density in a case the scanning was made at a total of 10 different values of the magnetic flux density B. Arrows in the figure indicate the positions x at which a dramatic increase of the $\tau_1$ was identified.

Figure 17:
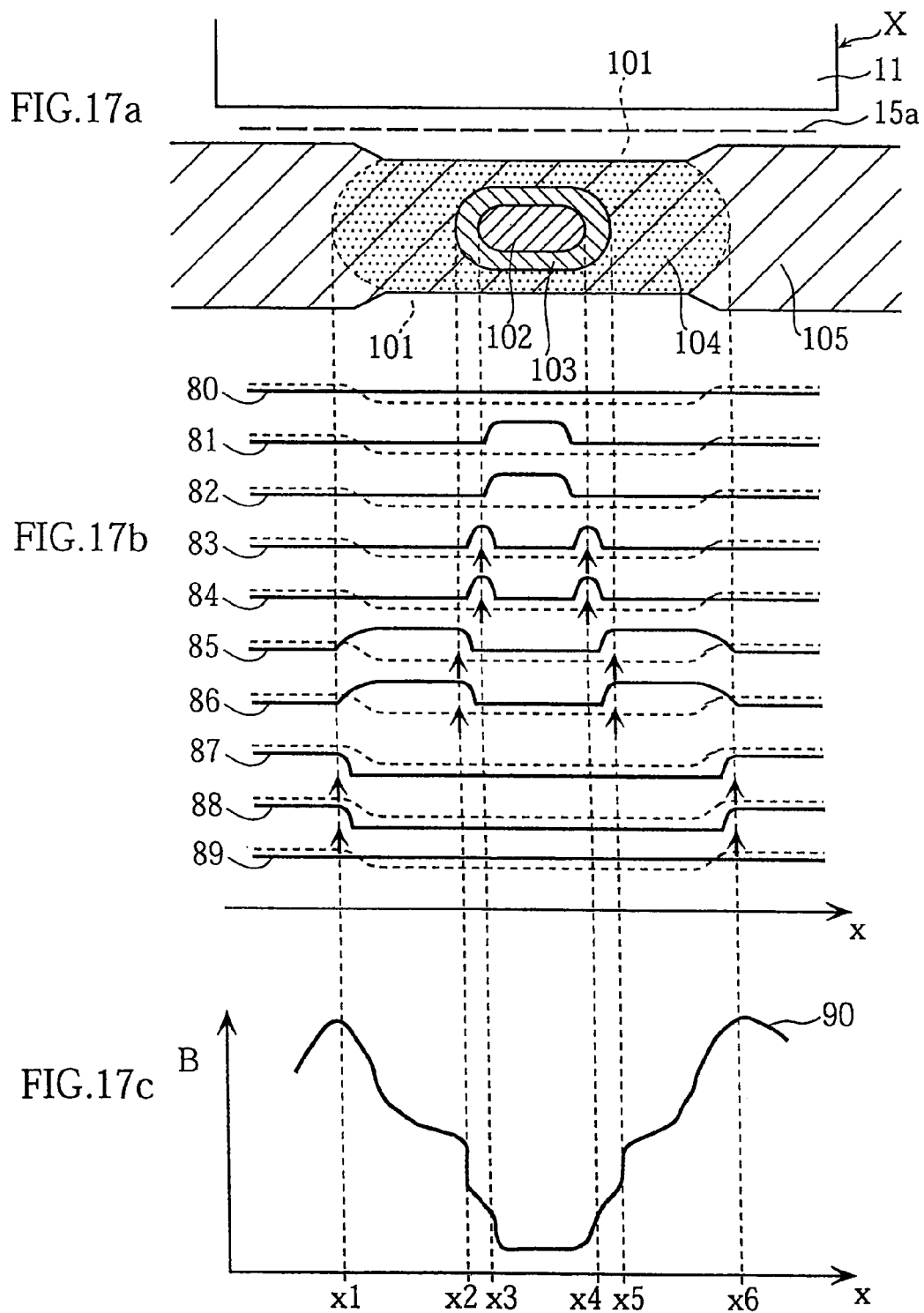
FIG. 17a through FIG. 17c illustrate a concept of non-destructive inspection method according to the second embodiment.
Figure 18:
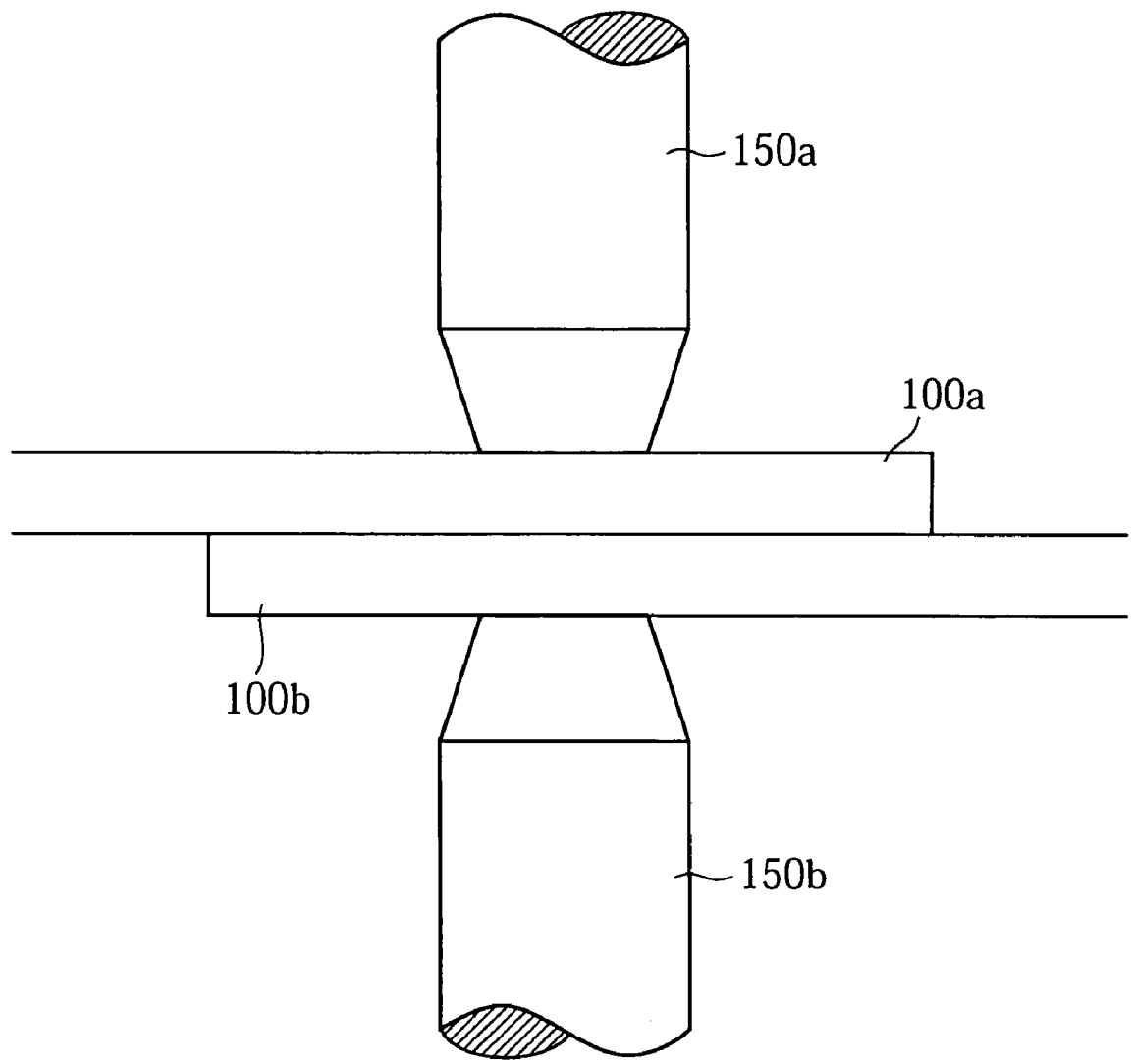
FIG. 18 is an illustration of spot welding.

Next, in Step S8', a magnetic flux density curve 90 with the measurement position x as a variable is obtained as shown in FIG. 17, based on the magnetic flux density data of the critical magnetostatic field identified in Step S7' where the time constant showed dramatic increase. The magnetic flux density curve 90 in FIG. 17 is a two-dimensional interpretation of the internal structure information of the spot weld section. Specifically, x1–x6 represents the HAZ diameter L4, x2–x5 represents the joint diameter L3, and x3–x4 represents the nugget diameter L2. The magnetic flux density curve 90 is displayed as necessary on the monitor of the data processing section 40.

Next, in Step S9', the lengths of x3–x4, x2–x5 and x1–x6 are calculated based on the data regarding the magnetic flux density curve 90, whereby a nugget diameter L2, a joint diameter L3 and a HAZ diameter L3 are given estimated values. Next, in Step S10', the estimated nugget diameter L2 is compared to a predetermined threshold value, to determine on the quality of welding of the spot weld section.

Each of the approximate curves 80–89 in FIG. 17b includes a component originated from the indentations 101. However, the magnetic flux density curve 90 in FIG. 17c is plotted in the coordinate system with the vertical axis representing the magnetic flux density that gives dramatic change in these curves, and does not include a component originated from the indentations 101. Therefore, the present embodiment makes it possible to obtain information about the internal structure appropriately regardless of the outside surface undulation in the spot weld section. It should be appreciated that FIG. 17b also shows magnetic flux density curves in broken lines, each based on the magnetic flux density distribution data at t=0 for each of the measurement positions, calculated in Step S5' in the cycles with the magnetic flux density being B3 through B4. Each of these magnetic flux density curve represents the surface waveform of the spot weld section, and these curves do not differ from each other throughout the cycles, indicating that the indentations 101 does not affect the magnetic flux density curve 90 in FIG. 17.

FIG. 17c shows a case in which the nugget diameter L2 is estimated to be the distance between the two inflection points of the magnetic flux density curve 90 at the lowest magnetic flux density. As to interpretation of a specific point in the inflection to be the border between the nugget section 102 and the pressure bonded section 103, it is preferable that the interpretation be made through a predetermined set of steps, on the basis of correlation data between the estimated nugget diameter L2 obtained from the inflection point data of the magnetic flux density curve 90 according to the present embodiment and actual measurement data of the nugget diameter L2.

In the first and the second embodiments, the results of measurements are not influenced by the indentations 101. As a result, it has become possible to make accurate estimation on the nugget diameter L2, and therefore to obtain highly reliable inspection results on the welding quality of spot weld sections. Further, it is also possible to obtain detailed information on the internal structure of the spot weld section, such as the joint diameter L3 and the HAZ diameter L4.

The present invention has been described above by taking an example of non-destructive inspection method for spot weld sections. The present invention is not limited to this, and is applicable also to non-destructive inspection apparatuses and methods for measuring and inspecting internal flaws, hardness, acting stresses and so on in steel members for example. The non-destructive inspection method according to the present invention has been described with reference to graphs and other visual representations, but it should be noted that various data processing and analyses can be made by means of arithmetic processing using a variety of mathematical functions equivalent to each of the graphs exhibited.

The invention claimed is:

1. A non-destructive inspection method including:
   a step of magnetizing an inspection target by applying a first magnetostatic field to the target;
   a step of shutting off the first magnetostatic field and measuring transient change in a differential magnetic flux density of a first residual magnetic field passing through the magnetized target, the measuring being performed at a plurality of measurement positions;
   a step of obtaining a first time constant provided by a main time constant of the transient change for each of the measurement positions;
   a step of magnetizing the target by applying a second magnetostatic field to the target;
   a step of shutting off the second magnetostatic field and measuring transient change in a differential magnetic flux density of a second residual magnetic field passing through the magnetized target, the measuring being performed at each of the measurement positions;
   a step of obtaining a second time constant provided by a main time constant of the transient change for each of the measurement positions; and
   an information obtaining step of obtaining information about an internal structure of the target based on a difference between distribution of the first time constant and distribution of the second time constant at the measurement positions;
   wherein the information about the internal structure in the information obtaining step is obtained based on a ratio function which is derived from a distribution function of the first time constant with the measurement position as a variable and a distribution function of the second time constant with the measurement position as a variable.

2. The method according to claim 1, wherein the measurement positions are in a row facing the target.

3. The method according to claim 1, wherein the target is a spot weld section in a jointed plate member made by spot welding two sheet metals.

4. The method according to claim 3, wherein the information obtained in the information obtaining step includes information about a shape of nugget section included in the spot weld section.

5. A non-destructive inspection method comprising:
   a scanning step including a cycle of magnetizing a target by applying a magnetostatic field to the target, shutting off the magnetostatic field to measure transient change in a differential magnetic flux density of a residual magnetic field which passes through the magnetized target at a plurality of measurement positions, and obtaining a main time constant of the transient change for each of the measurement positions, the cycle being repeatedly performed for each of a plurality of magnetostatic fields of different magnetic flux densities;
   an analyzing step of analyzing a change that the main time constant undergoes at each measurement position as the plurality of magnetostatic fields are changed in the scanning step; and
   an information obtaining step of obtaining information about an internal structure of the target based on an analysis result obtained by the analyzing step;
   wherein in the analyzing step, at each of the measurement positions, a magnetic flux density of a critical magnetostatic field is determined, for which field the change of the main time constant during the scanning step with respect to changes in the magnetostatic field achieves a maximum value, and wherein in the information obtaining step, information about the internal structure of the target is obtained based on a distribution function of the critical magnetostatic field with the measurement positions as a variable.

6. The method according to claim 5, wherein the measurement positions are in a row facing the target.

7. The method according to claim 5, wherein the target is a spot weld section in a jointed plate member made by spot welding two sheet metals.

8. The method according to claim 7, wherein the information about the internal structure obtained in the information obtaining step comprises information about a shape of a nugget section included in the spot weld section.

* * * * *